United States Patent
Campbell et al.

(10) Patent No.: US 6,923,827 B2
(45) Date of Patent: Aug. 2, 2005

(54) BALLOON CATHETER DEVICE

(75) Inventors: Carey V. Campbell, Flagstaff, AZ (US); Alvaro J. Laguna, Flagstaff, AZ (US); Mark S. Spencer, Phoenix, AZ (US)

(73) Assignee: Gore Enterprise Holdings, Inc., Newark, DE (US)

(*) Notice: Subject to any disclaimer, the term of this patent is extended or adjusted under 35 U.S.C. 154(b) by 14 days.

(21) Appl. No.: 10/300,056

(22) Filed: Nov. 20, 2002

(65) Prior Publication Data

US 2003/0074016 A1 Apr. 17, 2003

Related U.S. Application Data

(63) Continuation of application No. 09/252,322, filed on Feb. 18, 1999, now abandoned, which is a continuation of application No. 08/858,309, filed on May 19, 1997, now Pat. No. 6,120,477, which is a continuation-in-part of application No. 08/673,635, filed on Jun. 26, 1996, now Pat. No. 5,868,704, which is a continuation-in-part of application No. 08/532,905, filed on Sep. 18, 1995, now Pat. No. 5,752,934.

(51) Int. Cl.[7] ................................................. A61F 2/06
(52) U.S. Cl. ..................... 623/1.11; 606/194; 604/103; 604/103.05
(58) Field of Search ............................. 604/96.01–104, 604/507–510, 164.1; 606/108, 190–200; 623/1.1, 1.11–1.54, 11.11, 900, 902; 600/201, 204, 207, 210

(56) References Cited

U.S. PATENT DOCUMENTS

| | | |
|---|---|---|
| 3,953,566 A | 4/1976 | Gore |
| 4,003,382 A | 1/1977 | Dyke |
| 4,106,509 A | 8/1978 | McWhorter |
| 4,187,390 A | 2/1980 | Gore |
| 4,194,041 A | 3/1980 | Gore et al. |
| 4,279,245 A | 7/1981 | Takagi et al. |
| 4,304,010 A | 12/1981 | Mano |
| 4,403,612 A | 9/1983 | Fogarty |
| 4,443,511 A | 4/1984 | Worden et al. |
| 4,573,966 A | 3/1986 | Weikl et al. |
| 4,613,544 A | 9/1986 | Burleigh |
| 4,619,641 A | 10/1986 | Schanzer |
| 4,637,396 A | 1/1987 | Cook |
| 4,650,466 A | 3/1987 | Luther |
| 4,702,252 A | 10/1987 | Brooks et al. |
| 4,706,670 A | 11/1987 | Andersen et al. |
| 4,713,070 A | 12/1987 | Mano |
| 4,737,219 A | 4/1988 | Taller et al. |
| 4,739,762 A * | 4/1988 | Palmaz ..................... 623/1.11 |

(Continued)

FOREIGN PATENT DOCUMENTS

| | | |
|---|---|---|
| EP | 372088 | 6/1990 |
| WO | 9014054 | 11/1990 |
| WO | 94/02185 | 2/1994 |
| WO | 95/05555 | 2/1995 |
| WO | 95/09667 | 4/1995 |
| WO | 9614895 | 5/1996 |
| WO | 97/02791 | 1/1997 |

Primary Examiner—Glenn K. Dawson
(74) Attorney, Agent, or Firm—Morgan & Finnegan, L.L.P.; Wayne D. House; Kenneth H. Sonnenfeld

(57) ABSTRACT

Balloon catheters having the strength and maximum inflated diameter characteristics of an angioplasty balloon and having the recovery characteristics during deflation of an elastic embolectomy balloon. The balloon catheter can be made in very small sizes and has a lubricious and chemically inert outer surface. The balloon catheter is easy to navigate through tortuous passageways, is capable of rapid inflation and deflation and has high burst strengths. Balloon covers having these same characteristics are also described for use with conventional embolectomy balloons or angioplasty balloons.

4 Claims, 13 Drawing Sheets

U.S. PATENT DOCUMENTS

| | | | |
|---|---|---|---|
| 4,764,560 A | | 8/1988 | Mitchell |
| 4,816,339 A | | 3/1989 | Tu et al. |
| 4,832,688 A | | 5/1989 | Sagae et al. |
| 4,896,669 A | | 1/1990 | Bhate et al. |
| 4,946,464 A | | 8/1990 | Pevsner |
| 4,955,899 A | | 9/1990 | Dell Corna et al. |
| 5,066,298 A | | 11/1991 | Hess |
| 5,071,609 A | | 12/1991 | Tu et al. |
| 5,087,244 A | | 2/1992 | Wolinsky et al. |
| 5,100,429 A | * | 3/1992 | Sinofsky et al. ............ 623/1.21 |
| 5,112,304 A | | 5/1992 | Barlow et al. |
| 5,116,318 A | | 5/1992 | Hillstead |
| 5,152,782 A | | 10/1992 | Kowligi et al. |
| 5,192,296 A | | 3/1993 | Bhate et al. |
| 5,197,978 A | * | 3/1993 | Hess ......................... 623/1.18 |
| 5,201,706 A | | 4/1993 | Noguchi et al. |
| 5,213,576 A | | 5/1993 | Abiuso et al. |
| 5,236,659 A | | 8/1993 | Pinchuk et al. |
| 5,254,090 A | | 10/1993 | Lombardi et al. |
| 5,256,143 A | | 10/1993 | Miller et al. |
| 5,286,254 A | | 2/1994 | Shapland et al. |
| 5,290,306 A | * | 3/1994 | Trotta et al. ................. 606/194 |
| 5,342,348 A | * | 8/1994 | Kaplan .................... 604/891.1 |
| 5,348,538 A | | 9/1994 | Wang et al. |
| 5,358,486 A | | 10/1994 | Saab |
| 5,358,516 A | | 10/1994 | Myers et al. |
| 5,366,442 A | | 11/1994 | Wang et al. |
| 5,403,340 A | | 4/1995 | Wang et al. |
| 5,409,495 A | * | 4/1995 | Osborn ...................... 623/1.11 |
| 5,415,636 A | | 5/1995 | Forman |
| 5,425,710 A | | 6/1995 | Khair et al. |
| 5,429,605 A | | 7/1995 | Richling |
| 5,456,661 A | | 10/1995 | Narciso |
| 5,458,568 A | | 10/1995 | Racchini et al. |
| 5,458,605 A | * | 10/1995 | Klemm ....................... 606/108 |
| 5,466,252 A | | 11/1995 | Soukup et al. |
| 5,470,313 A | | 11/1995 | Crocker et al. |
| 5,478,320 A | | 12/1995 | Trotta |
| 5,478,349 A | * | 12/1995 | Nicholas .................... 623/1.11 |
| 5,490,839 A | | 2/1996 | Wang et al. |
| 5,496,276 A | | 3/1996 | Wang et al. |
| 5,498,238 A | | 3/1996 | Shapland et al. |
| 5,499,980 A | | 3/1996 | Euteneuer |
| 5,499,995 A | | 3/1996 | Teirstein |
| 5,500,180 A | | 3/1996 | Anderson et al. |
| 5,500,181 A | | 3/1996 | Wang et al. |
| 5,512,051 A | | 4/1996 | Wang et al. |
| 5,519,172 A | | 5/1996 | Spencer et al. |
| 5,527,282 A | | 6/1996 | Segal |
| 5,529,820 A | | 6/1996 | Nomi et al. |
| 5,609,605 A | | 3/1997 | Marshall et al. |
| 5,613,979 A | | 3/1997 | Trotta et al. |
| 5,620,649 A | | 4/1997 | Trotta |
| 5,641,373 A | | 6/1997 | Shannon et al. |
| 5,647,848 A | | 7/1997 | Jorgensen |
| 5,716,396 A | * | 2/1998 | Williams, Jr. .............. 623/1.22 |
| 5,752,934 A | * | 5/1998 | Campbell et al. ......... 604/96.01 |
| 5,766,201 A | | 6/1998 | Ravenscroft et al. |
| 5,797,877 A | | 8/1998 | Hamilton et al. |
| 5,807,327 A | | 9/1998 | Green et al. |
| 5,951,941 A | | 9/1999 | Wang et al. |
| 6,287,314 B1 | | 9/2001 | Lee et al. |
| 6,319,249 B1 | | 11/2001 | Lee et al. |
| 6,319,259 B1 | * | 11/2001 | Lee et al. ................... 606/108 |
| 2002/0087165 A1 | | 7/2002 | Lee et al. |

* cited by examiner

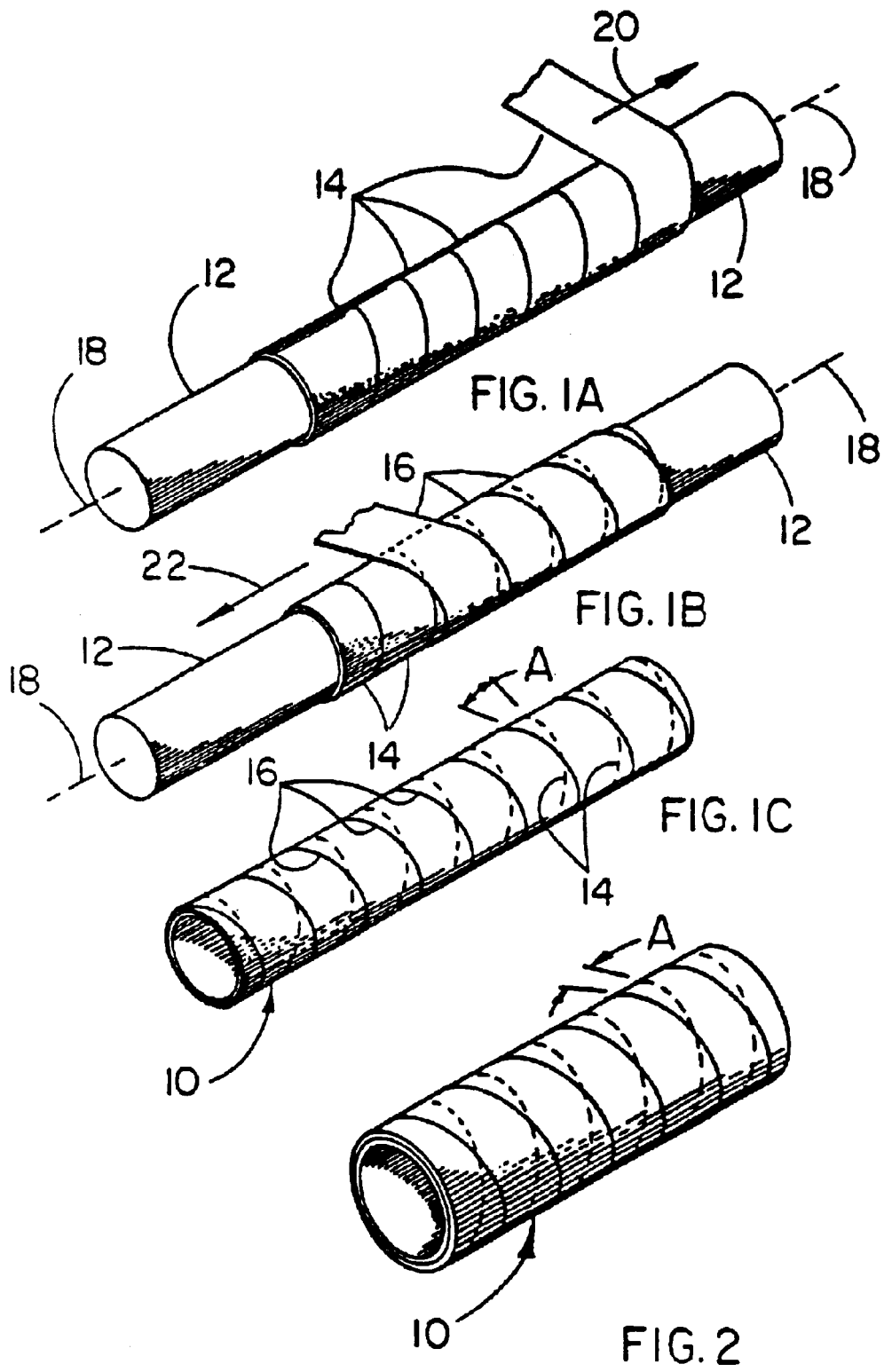

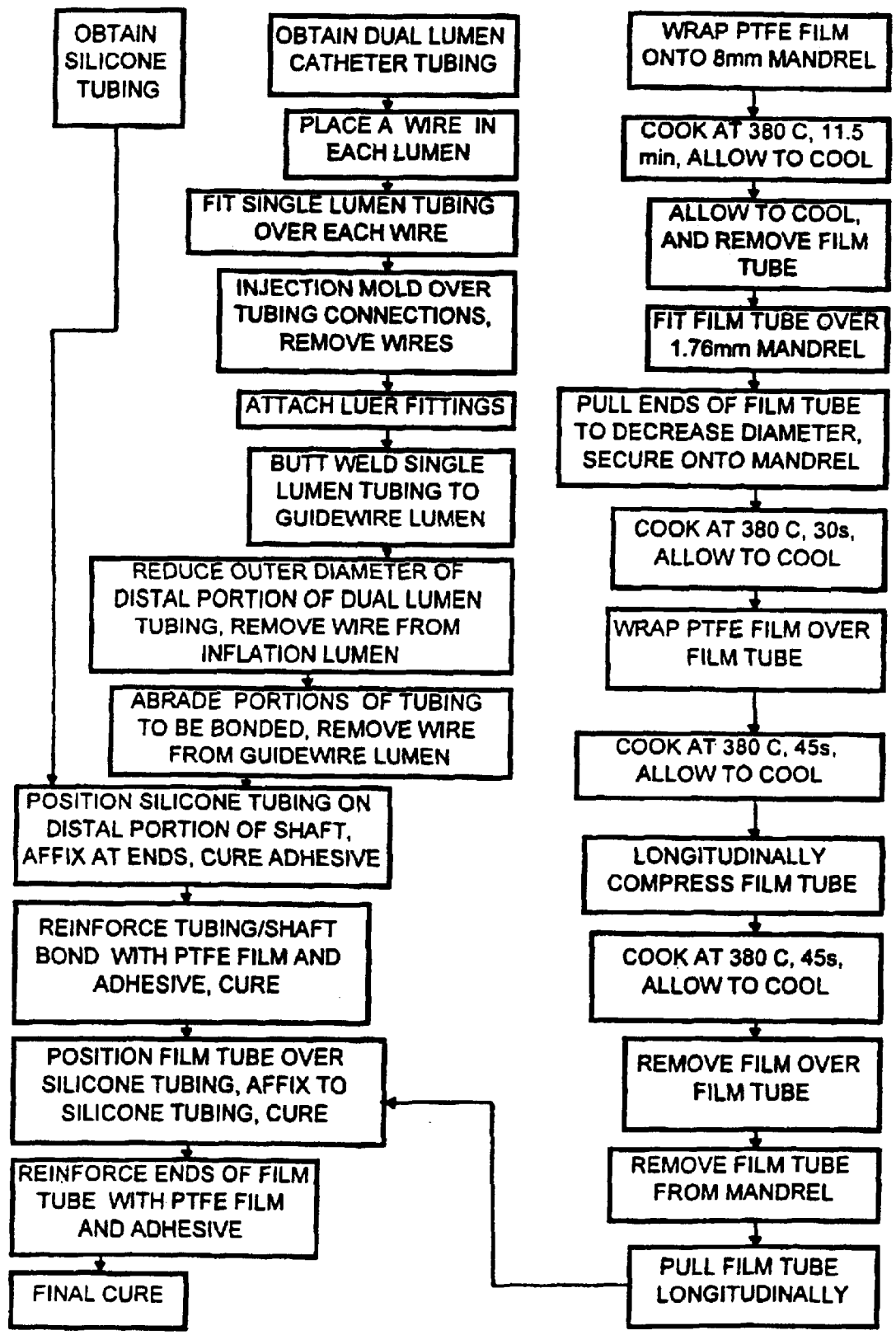
FIGURE 10F: EXAMPLE 7 FLOW CHART

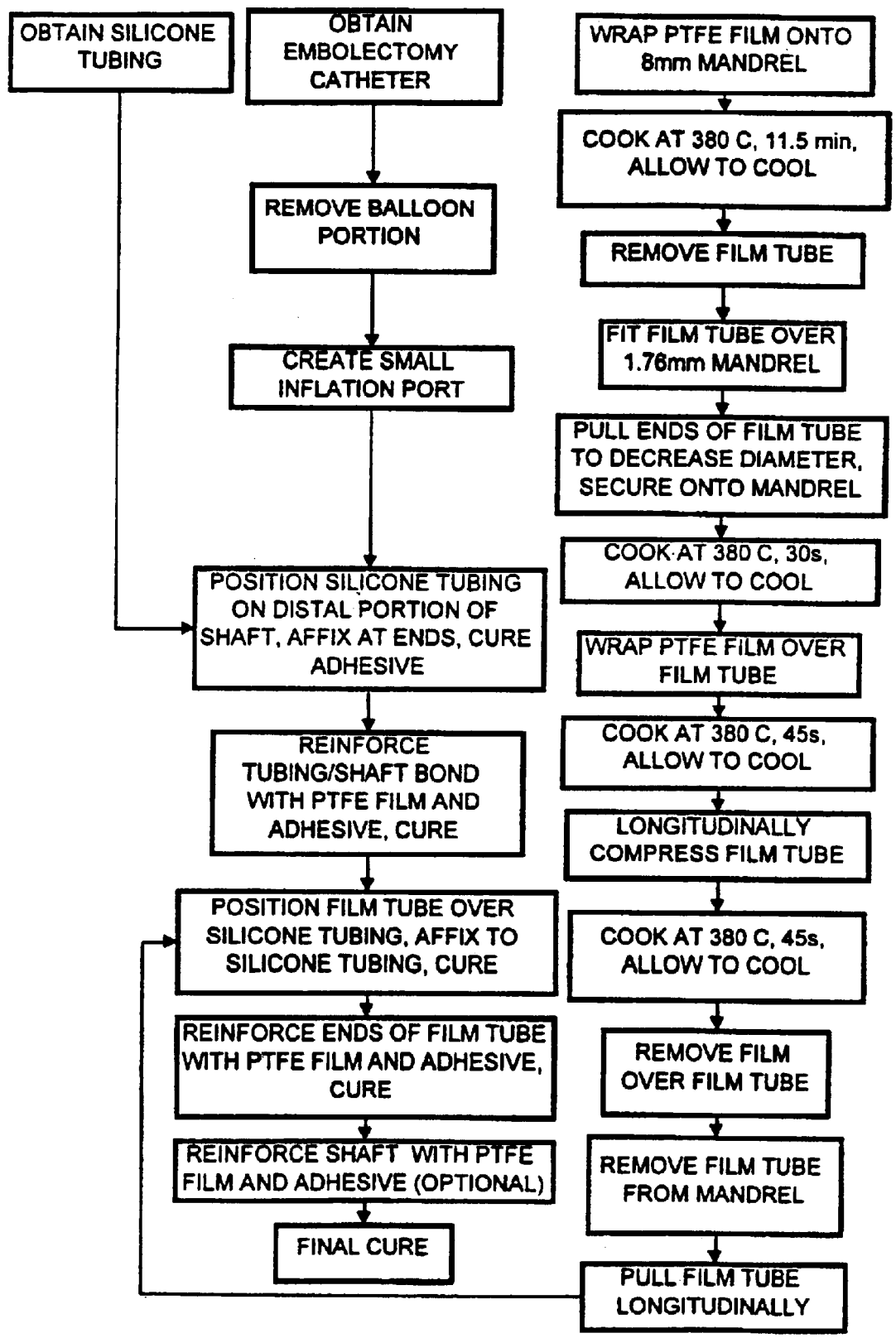
FIGURE 11C: EXAMPLE 8 FLOW CHART

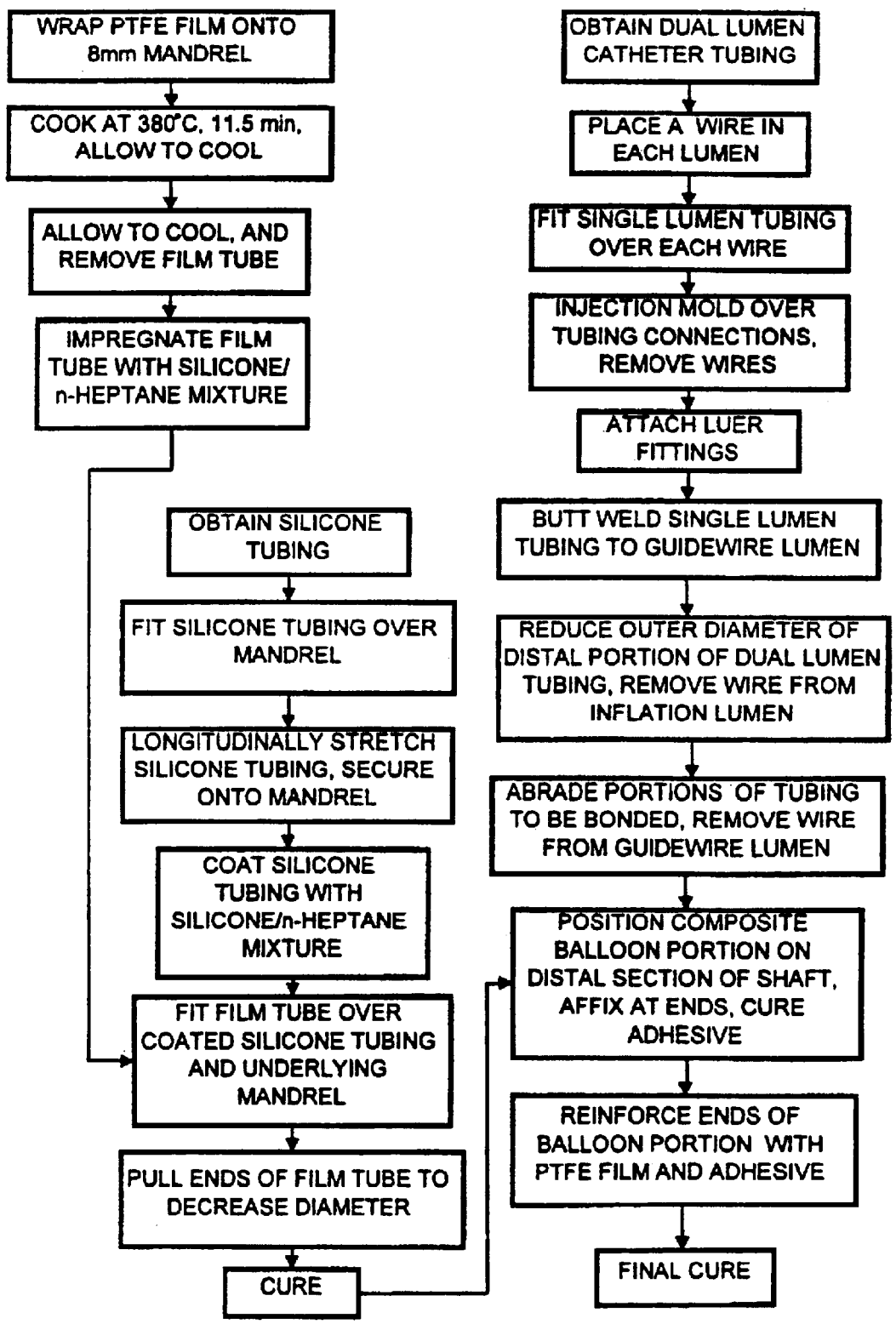
FIGURE 12C: EXAMPLE 9 FLOW CHART

BALLOON CATHETER DEVICE

CROSS REFERENCE TO RELATED APPLICATIONS

This application is a continuation of application Ser. No. 09/252,322, filed Feb. 18, 1999 now abandoned which is a continuation of application Ser. No. 08/858,309 filed May 19, 1997 now U.S. Pat. No. 6,120,477 which is a continuation-in-part of application Ser. No. 08/673,635 filed Jun. 26, 1996 now U.S. Pat. No. 5,868,704 which is a continuation-in-part of application Ser. No. 08/532,905 filed Sep. 18, 1995 now U.S. Pat. No. 5,752,934.

FIELD OF THE INVENTION

The present invention relates to catheter balloons used in a variety of surgical procedures and to balloon covers for use with catheter balloons.

BACKGROUND OF THE INVENTION

Balloon catheters of various forms are commonly employed in a number of surgical procedures. These devices comprise a thin catheter tube that can be guided through a body conduit of a patient such as a blood vessel and a distensible balloon located at the distal end of the catheter tube. Actuation of the balloon is accomplished through use of a fluid filled syringe or similar device that can inflate the balloon by filling it with fluid (e.g., water or saline solution) to a desired degree of expansion and then deflate the balloon by withdrawing the fluid back into the syringe.

In use, a physician will guide the balloon catheter into a desired position and then expand the balloon to accomplish the desired result (e.g., clear a blockage, or install or actuate some other device). Once the procedure is accomplished, the balloon is then deflated and withdrawn from the blood vessel.

There are two main forms of balloon catheter devices. Angioplasty catheters employ a balloon made of relatively strong but generally inelastic material (e.g., polyester) folded into a compact, small diameter cross section. These relatively stiff catheters are used to compact hard deposits in vessels. Due to the need for strength and stiffness, these devices are rated to high pressures, usually up to about 8 to 12 atmospheres depending on rated diameter. They tend to be self-limiting as to diameter in that they will normally distend up to the rated diameter and not distend appreciably beyond this diameter until rupture due to over-pressurization. While the inelastic material of the balloon is generally effective in compacting deposits, it tends to collapse unevenly upon deflation, leaving a flattened, wrinkled bag, substantially larger in cross section than the balloon was when it was originally installed. Because of their tendency to assume a flattened cross section upon inflation and subsequent deflation, their deflated maximum width tends to approximate a dimension corresponding to one-half of the rated diameter times pi. This enlarged, wrinkled bag may be difficult to remove, especially from small vessels. Further, because these balloons are made from inelastic materials, their time to complete deflation is inherently slower than elastic balloons.

By contrast, embolectomy catheters employ a soft, very elastic material (e.g., natural rubber latex) as the balloon. These catheters are employed to remove soft deposits, such as thrombus, where a soft and tacky material such as latex provides an effective extraction means. Latex and other highly elastic materials generally will expand continuously upon increased internal pressure until the material bursts. As a result, these catheters are generally rated by volume (e.g., 0.3 cc) in order to properly distend to a desired size. Although relatively weak, these catheters do have the advantage that they tend to readily return to their initial size and dimensions following inflation and subsequent deflation.

Some catheter balloons constructed of both elastomeric and non-elastomeric materials have been described previously. U.S. Pat. No. 4,706,670 describes a balloon dilatation catheter constructed of a shaft made of an elastomeric tube and reinforced with longitudinally inelastic filaments. This device incorporates a movable portion of the shaft to enable the offset of the reduction in length of the balloon portion as the balloon is inflated. The construction facilitates the inflation and deflation of the balloon.

While balloon catheters are widely employed, currently available devices experience a number of shortcomings. First, as has been noted, the strongest materials for balloon construction tend to be relatively inelastic. The flattening of catheter balloons made from inelastic materials that occurs upon inflation and subsequent deflation makes extraction and navigation of a deflated catheter somewhat difficult. Contrastly, highly elastic materials tend to have excellent recovery upon deflation, but are not particularly strong when inflated nor are they self-limiting to a maximum rated diameter regardless of increasing pressure. This severely limits the amount of pressure that can be applied with these devices. It is also somewhat difficult to control the inflated diameter of these devices.

Second, in instances where the catheter is used to deliver some other device into the conduit, it is particularly important that a smooth separation of the device and the catheter balloon occur without interfering with the placement of the device. Neither of the two catheter devices described above is ideal in these instances. A balloon that does not completely compact to its original size is prone to snag the device causing placement problems or even damage to the conduit or balloon. Similarly, the use of a balloon that is constructed of tacky material will likewise cause snagging problems and possible displacement of the device. Latex balloons are generally not used for device placement in that they are considered to have inadequate strength for such use. Accordingly, it is a primary purpose of the present invention to create a catheter balloon that is small and slippery for initial installation, strong for deployment, and returns to its compact size and dimensions for ease in removal and further navigation following deflation. It is also believed desirable to provide a catheter balloon that will remain close to its original compact pre-inflation size even after repeated cycles of inflation and deflation. Other primary purposes of the present invention are to strengthen elastic balloons, to provide them with distension limits and provide them with a lubricious outer surface. The term "deflation" herein is used to describe a condition subsequent to inflation. "Pre-inflation" is used to describe the condition prior to initial inflation.

SUMMARY OF THE INVENTION

The present invention is an improved balloon catheter device for use in a variety of surgical procedures. The balloon catheter device of the present invention comprises a catheter tube having a continuous lumen connected to an inflatable and deflatable balloon at one end of the catheter tube. The catheter tube may have additional lumens provided for other purposes. The balloon can have a burst strength equal to or greater than that of conventional PTA catheter balloons. The balloon also has a maximum inflation diameter in a similar fashion to conventional PTA catheter balloons. The inventive balloon offers the recovery characteristics of a latex balloon that when deflated is of about the same maximum diameter as it was prior to inflation. This allows the inventive balloon to be withdrawn following deflation more easily than conventional PTA balloons which assume a flattened, irregular cross section following deflation and so have a deflated maximum diameter much larger than the pre-inflation maximum diameter. The balloon also has a smooth and lubricious surface which also aids in insertion and withdrawal. The inventive balloon possesses all of the above attributes even when made in small sizes heretofore commercially unavailable in balloon catheters without a movable portion of the catheter shaft or some other form of mechanical assist. The present invention eliminates the need for a movable portion of the shaft and associated apparatuses to aid in balloon deflation.

The present invention is made from polytetrafluoroethylene (hereinafter PTFE) materials and elastomeric materials. The PTFE is preferably porous PTFE made as taught by U.S. Pat. Nos. 3,953,566 and 4,187,390, both of which are incorporated by reference herein. An additional optional construction step, longitudinally compressing a porous PTFE tube prior to addition of the elastomeric component, allows the balloon or balloon cover to sufficiently change in length to enable the construction of higher pressure balloons, again without the need for mechanical assist. Particularly small sizes (useful in applications involving small tortuous paths such as is present in brain, kidney, and liver procedures) can be achieved by decreasing the wall thickness of the balloon via impregnation of a porous PTFE tube with silicone adhesive, silicone elastomer, silicone dispersion, polyurethane or another suitable elastomeric material instead of using a separate elastomeric member. Impregnation involves at least partially filling the pores of the porous PTFE. The pores (void spaces) are considered to be the space or volume within the bulk volume of the porous PTFE material (i.e., within the overall length, width and thickness of the of the porous PTFE material) not occupied by PTFE material. The void spaces of the porous PTFE material from which the balloon is at least partially constructed may be substantially sealed in order that the balloon is liquid-tight at useful pressures by either the use of a separate tubular elastomeric substrate in laminated relationship with the porous PTFE, or by impregnation of the void spaces of the porous PTFE with elastomeric material, or by both methods. U.S. Pat. No. 5,519,172 teaches in detail the impregnation of porous PTFE with elastomers. In that this patent relates primarily to the construction of a jacket material for the protection of electrical conductors, the suitability of each of the various described materials for in vivo use as catheter balloon materials must be considered.

The balloon may be made from the materials described herein as a complete, stand-alone balloon or alternatively may be made as a cover for either conventional polyester PTA balloons or for latex embolectomy balloons. The use of the balloon cover of the present invention provides the covered balloon, regardless of type, with the best features of conventional PTA balloons and renders viable the use of elastic balloons for PTA procedures. That is to say, the covered balloon will have high burst strength, a predetermined maximum diameter, the ability to recover to substantially its pre-inflation size following deflation, and a lubricious exterior surface (unless it is desired to construct the balloon such that the elastomeric material is present on the outer surface of the balloon). The balloon cover substantially reduces the risk of rupture of an elastic balloon. Further, if rupture of the underlying balloon should occur, the presence of the balloon cover may serve to contain the fragments of the ruptured balloon. Still further, the inventive balloon and balloon cover can increase the rate of deflation of PTA balloons thereby reducing the time that the inflated balloon occludes the conduit in which it resides.

The present invention also enables the distension of a vessel and side branch or even a prosthesis within a vessel and its side branch without exerting significant force on the vessel or its branch. Further, it has been shown to be useful for flaring the ends of prostheses, thereby avoiding unwanted constrictions at the ends of the prostheses. Prostheses can slip along the length of prior art balloons during distension; the present invention not only reduces such slippage, it also can be used to create a larger diameter at the end of the graft than prior art materials.

The inventive balloon and balloon cover also maintain a substantially circular cross section during inflation and deflation in the absence of external constraint. Plus, the balloon and balloon cover can be designed to inflate at lower pressure in one portion of the length than another. This can be accomplished, for example, by altering the thickness of the elastomer content along the length of the balloon in order to increase the resistance to distension along the length of the balloon. Alternatively, the substrate tube may be constructed with varying wall thickness or varying amounts of helically-applied film may be applied along the tube length in order to achieve a similar effect.

The balloon catheter according to the present invention has opposing ends affixed to the catheter by opposing securing means. The balloon has a length measured between the opposing ends wherein the length preferably varies less than about ten percent, and more preferably less than about five percent, between when the balloon is in a deflated state and when the balloon is inflated to a pressure of eight atmospheres.

Balloons of the present invention can also be constructed to elute fluids at pressures exceeding the balloon inflation pressure. Such balloons could have utility in delivering drugs inside a vessel.

A catheter balloon of the present invention is anticipated to be particularly useful for various surgical vascular procedures, including graft delivery, graft distension, stent delivery, stent distension, and angioplasty. It may have additional utility for various other surgical procedures such as, for example, supporting skeletal muscle left ventricular assist devices during the healing and muscle conditioning period and as an intra-aortic balloon.

BRIEF DESCRIPTION OF THE DRAWINGS

FIGS. 1A, 1B and 1C are perspective views describing manufacture of the tubular component forming the balloon or balloon cover of the present invention.

FIG. 2 is a perspective view describing the tubular component as it appears when inflated.

FIGS. 10A–10F describe the construction of an alternative embodiment of a balloon catheter of the present invention wherein the balloon has separate substrate layers of an elastomeric material and a porous PTFE material in laminated relationship and wherein each end of each substrate material is separately affixed to a catheter shaft by separate wrappings of porous PTFE film.

FIGS. 11A, 11B and 11C describe the construction of an alternative embodiment of a balloon catheter of the present invention similar to that of FIGS. 10A–10F wherein a catheter shaft is used which comprises a tubular elastomeric material provided with a reinforcing wrapping of porous PTFE film.

FIGS. 12A, 12B and 12C describe the construction of an alternative embodiment of a balloon catheter of the present invention wherein a laminated tube of separate substrates of an elastomeric material and helically wrapped porous PTFE film are affixed to a catheter shaft by a wrapping of porous PTFE film at each end of the laminated tube.

DETAILED DESCRIPTION OF THE INVENTION

Figure 3A:
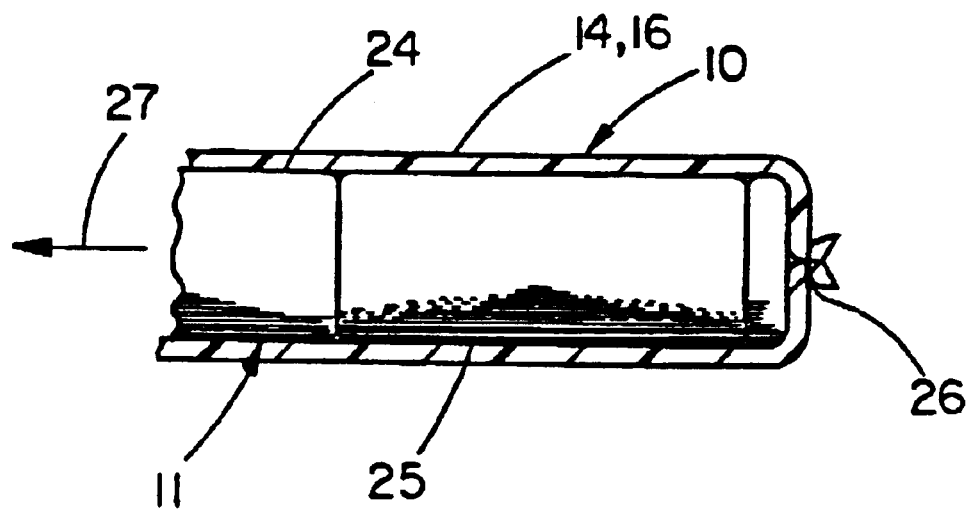
FIGS. 3A and 3B describe longitudinal cross sectional views of a balloon cover of the present invention without elastomer.

The catheter balloon and catheter balloon cover of the present invention are preferably made from porous PTFE films having a microstructure of interconnected fibrils. These films are made as taught by U.S. Pat. Nos. 3,953,566 and 4,187,390. The balloon and balloon cover may also incorporate a porous PTFE substrate tube in the form, for example, of an extruded and expanded tube or a tube constructed of film containing at least one seam. Also, the balloon may be impregnated with an elastomeric material.

To form the balloon or balloon cover, both of which are made in the shape of a tube, a thin, porous PTFE film of the type described above is slit into relatively narrow lengths. The slit film is helically wrapped onto the surface of a mandrel in two opposing directions, thereby forming a tube of at least two layers. FIGS. 1A, 1B and 1C describe this procedure. FIG. 1A shows the first layer 14 of porous PTFE film helically wrapped over the mandrel 12 with the traverse direction of the wrap applied in a first direction 20 parallel to the longitudinal axis 18. The longitudinal axis of a balloon is defined as coincident with the longitudinal axis of the balloon catheter shaft, that is along the length of the shaft. Substantially parallel is defined as between about 0° and 45°, or between about 135° and 180°, with respect to the longitudinal axis of the catheter shaft and substantially circumferential is defined as between about 45° and 135° with respect to the longitudinal axis of the catheter shaft. FIG. 1B describes the application of the second layer of porous PTFE film 16 helically wrapped over the top of the first layer 14, wherein second layer 16 is wrapped in a second traverse direction 22 parallel to longitudinal axis 18 and opposite to the first traverse direction 20.

Preferably both layers 14 and 16 are wrapped with the same pitch angle measured with respect to the longitudinal axis but measured in opposite directions. If, for example, film layers 14 and 16 are applied at pitch angles of 70° measured from opposite directions with respect to longitudinal axis 18, then included angle A between both 70° pitch angles is 40°.

More than two layers of helically wrapped film may be applied. Alternate layers of film should be wrapped from opposing directions and an even number of film layers should be used whereby an equal number of layers are applied in each direction.

Following completion of film wrapping, the helically wrapped mandrel is placed into an oven for suitable time and temperature to cause adjacent layers to heat-bond together. After removal from the oven and subsequent cooling, the resulting film tube may be removed from the mandrel. The film tube is next placed over the balloon, tensioned longitudinally and affixed in place over the balloon.

During use, the inflated balloon or balloon cover 10 of the present invention has an increased diameter which results in included angle A being substantially reduced as shown by FIG. 2. The balloon or balloon cover thus reaches its pre-determined diametrical limit as included angle A approaches zero.

The inventive balloon or balloon cover 10 is reduced in diameter following deflation by one of two ways. First, tension may be applied to the balloon or balloon cover parallel to longitudinal axis 18 to cause it to reduce in diameter following deflation to the form described by FIG. 1C. The application of tension is necessary if low profile is desired. Alternatively, a layer of elastomer, applied to the luminal surface of the balloon 10 and allowed to cure prior to use of the balloon, will cause the balloon to retract to substantially its pre-inflation size shown by FIG. 1C following deflation. The elastomer may take the form of a coating of elastomer applied directly to the luminal surface of the balloon or balloon cover 10, or an elastomeric balloon such as a latex balloon or a silicone tube may be adhered to the luminal surface of the inventive balloon 10 by the use of an elastomeric adhesive. Alternatively, elastomer can be impregnated into the porous material to create a balloon or balloon cover.

Figure 3B:
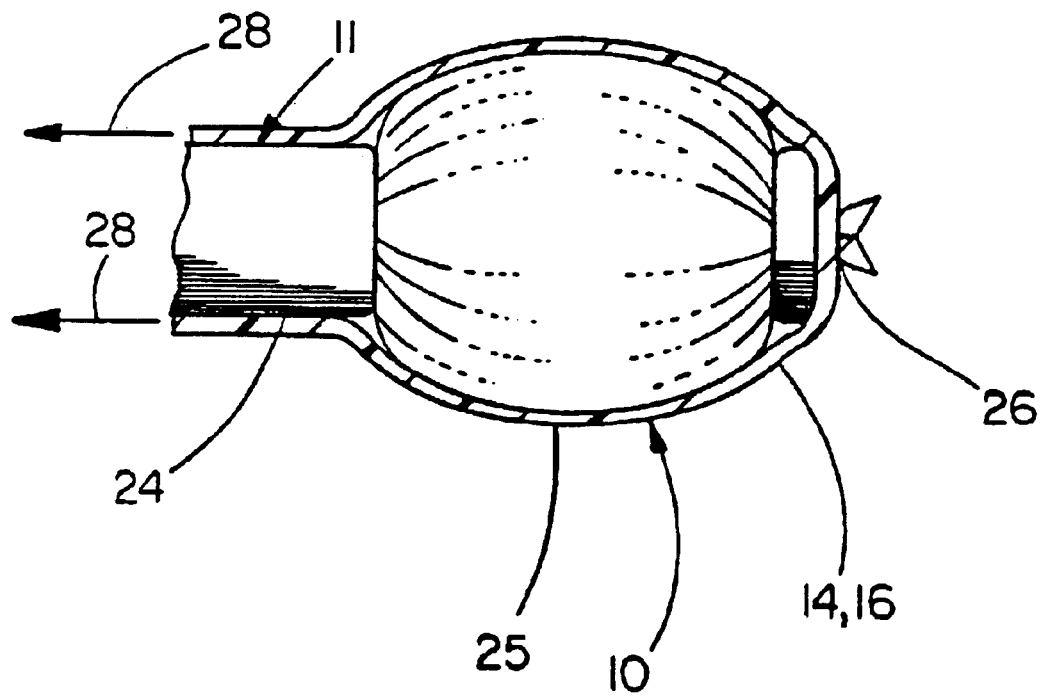
Figure 4A:
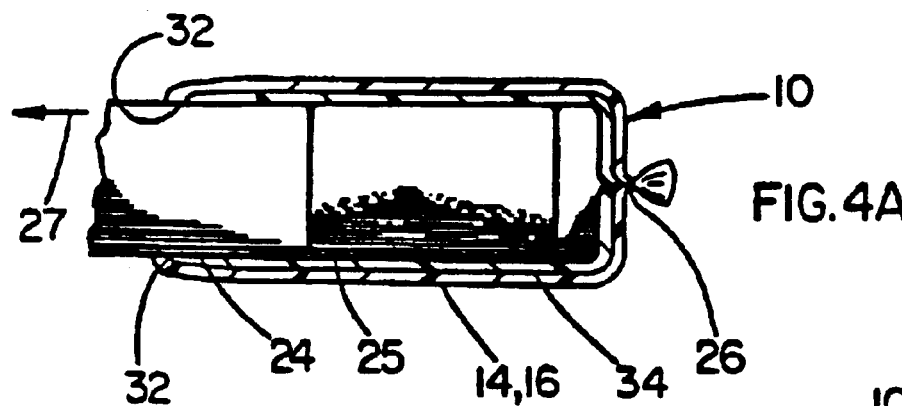
FIGS. 4A and 4B describe longitudinal cross sectional views of a balloon cover of the present invention incorporating a layer of elastomer.
Figure 4B:
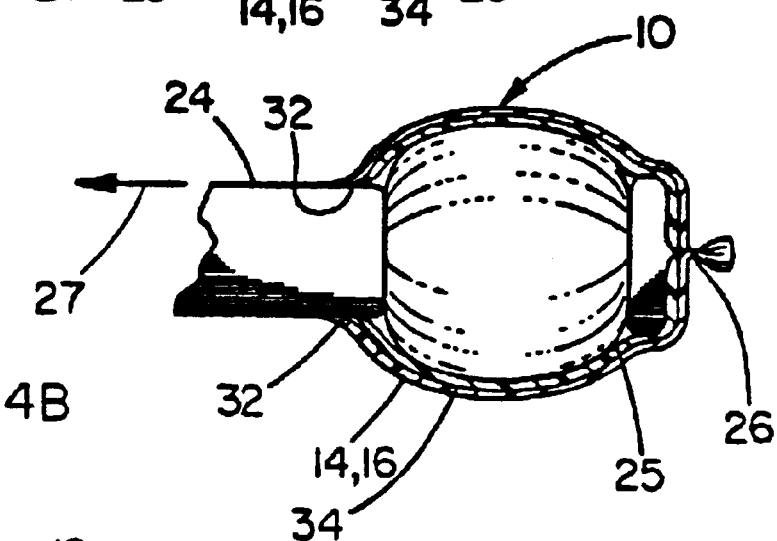

FIG. 3A describes a cross sectional view of a balloon cover 10 of the present invention in use with a conventional balloon catheter of either the angioplasty or embolectomy type. The figure describes a balloon cover without an elastomeric luminal coating. The balloon cover 10 is closed at distal end 26 of the balloon catheter 11. Balloon cover 10 extends in length part of the way to the proximal end 27 of balloon catheter 11 whereby balloon cover 10 completely covers catheter balloon 25 and at least a portion of the catheter 11. FIG. 3B describes the same balloon catheter 11 with catheter balloon 25 in an inflated state. Layers 14 and 16 of balloon cover 10 allow the cover to increase in diameter along with catheter balloon 25. During or following deflation of catheter balloon 25, tension is applied to the balloon cover 10 at the proximal end 27 of balloon catheter 11 as shown by arrows 28, thereby causing balloon cover 10 to reduce in diameter and substantially return to the state described by FIG. 3A. FIG. 4A describes a cross sectional view of a balloon cover 10 of the present invention wherein the balloon cover 10 has a liquid-tight layer of elastomer 34 applied to the inner surface of helically wrapped porous PTFE film layers 14 and 16. Balloon cover 10 is closed at distal end 26. The figure describes a ligated closure, such as by a thread or filament, however, other suitable closing means may be used. Proximal end 27 of balloon cover 10 is affixed to the distal end 32 of catheter 24. Balloon 25 may be of either the angioplasty or embolectomy type. If an elastomeric embolectomy balloon is used, it is preferred that the cover be adhered to the balloon by the use of an elastomeric adhesive to liquid-tight layer of elastomer 34. During inflation of balloon 25 as shown by FIG. 4B, helically wrapped porous PTFE film layers 14 and 16 and liquid-tight elastomer layer 34 increase in diameter along with balloon 25. During subsequent deflation, liquid-tight elastomer layer 34 causes helically wrapped porous PTFE film layers 14 and 16 to reduce in diameter as described previously, thereby returning substantially to the state described by FIG. 4A.

Figure 5A:
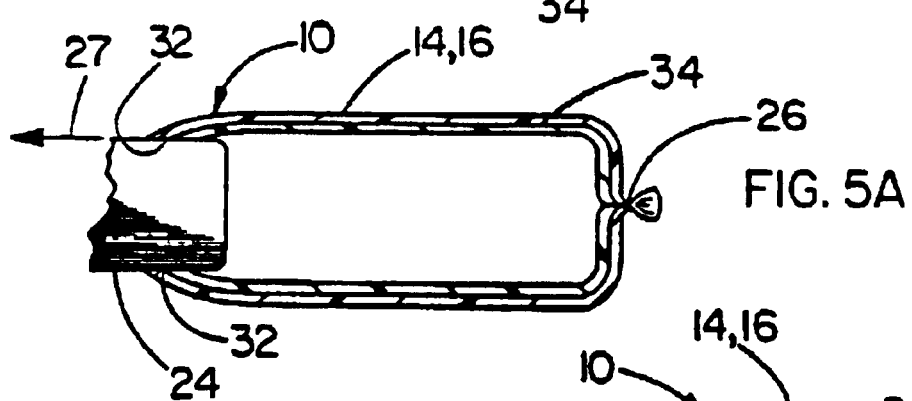
FIGS. 5A and 5B describe longitudinal cross sectional views of a catheter balloon of the present invention having the same material construction as the balloon cover of FIGS. 4A and 4B.
Figure 5B:
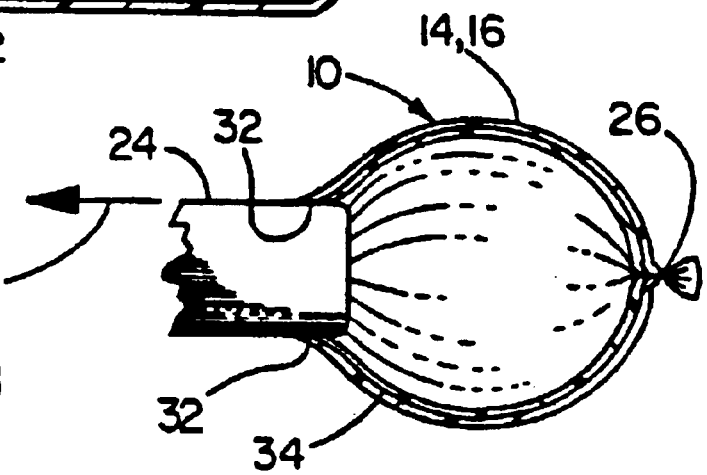

FIGS. 5A and 5B describe cross sectional views of a catheter balloon 10 made in the same fashion as the balloon cover described by FIGS. 4A and 4B. The presence of liquid-tight elastomer layer 34 allows this construction to function as an independent balloon 42 as described previously without requiring a conventional angioplasty or embolectomy balloon.

Figure 6A:
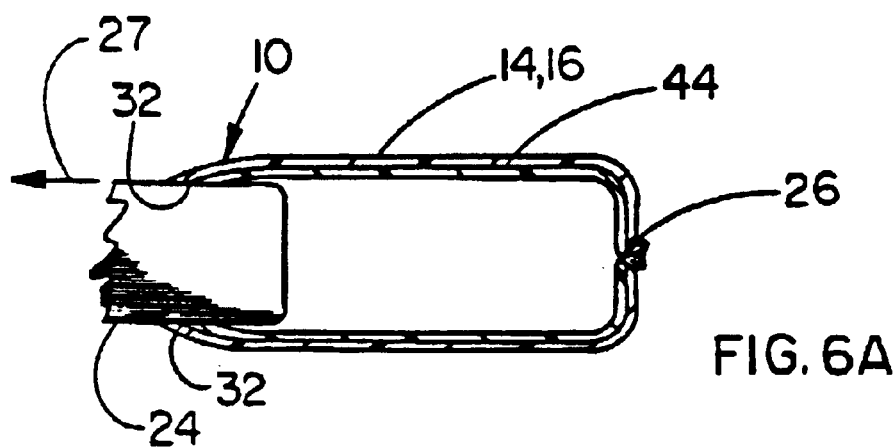
FIGS. 6A, 6B and 6C describe longitudinal cross sectional views of a catheter balloon of the type described by FIGS. 5A and 5B using a non-elastomeric material in place of the layer of elastomer.
Figure 6B:
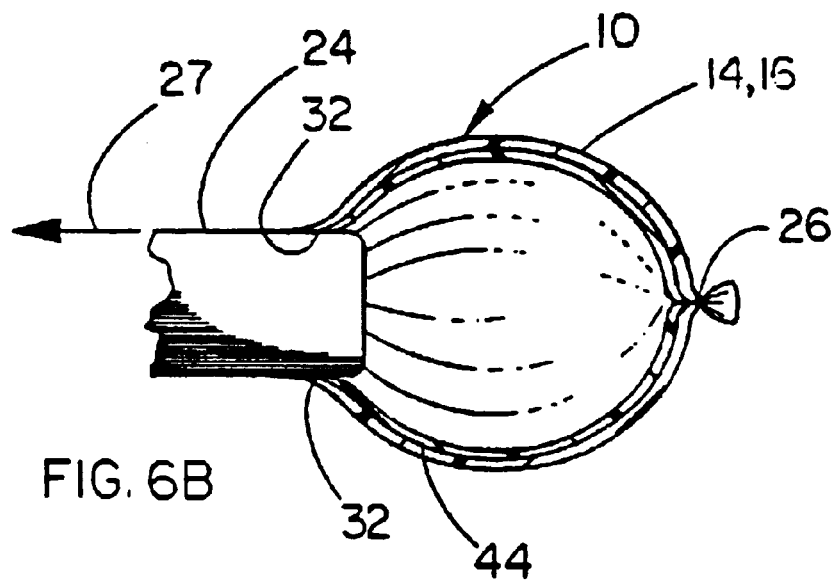
Figure 6C:
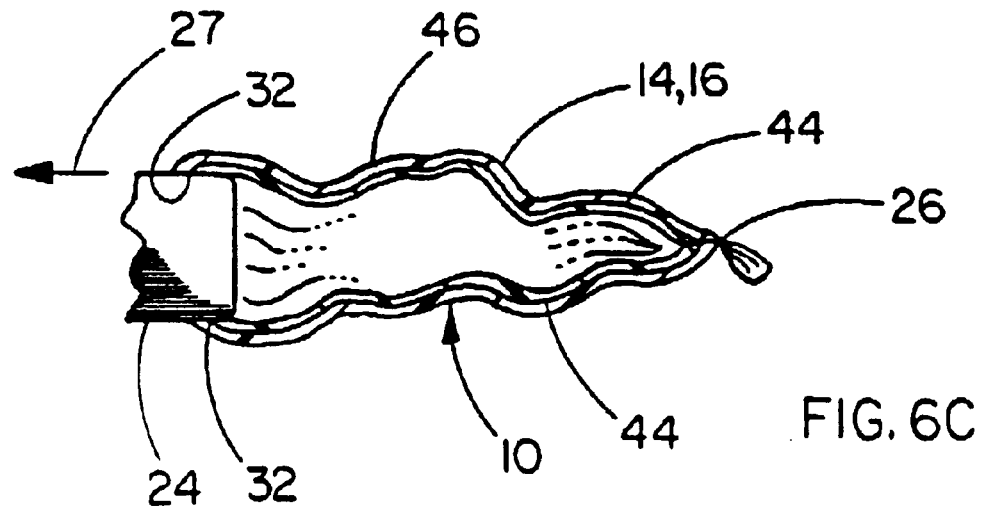

FIGS. 6A, 6B and 6C describe cross sectional views of an alternative embodiment of the catheter balloon 10 of the present invention. According to this embodiment helically wrapped porous PTFE film layers 14 and 16 are provided with a luminal coating 44 which is liquid-tight but is not elastomeric. The resulting balloon behaves in the fashion of a conventional angioplasty balloon but offers the advantages of a lubricious and chemically inert exterior surface. FIG. 6A describes the appearance of the balloon prior to inflation. FIG. 6B describes the balloon in an inflated state. As shown by FIG. 6C, following deflation, collapsed balloon 46 has a somewhat wrinkled appearance and an irregular transverse cross section in the same fashion as a conventional angioplasty balloon made from polyester or similar inelastic material.

It is also anticipated that the balloon and balloon cover of the present invention may be provided with an additional reinforcing mesh or braid on the exterior or interior surface of the balloon (or balloon cover), or more preferably between layers of the film whereby the mesh or braid is in the middle.

Alternatively, a mesh or braid of PTFE may be used as a balloon cover without including a continuous tube. A continuous tube does not include openings through its wall as does a conventional mesh or braid.

Figure 7:
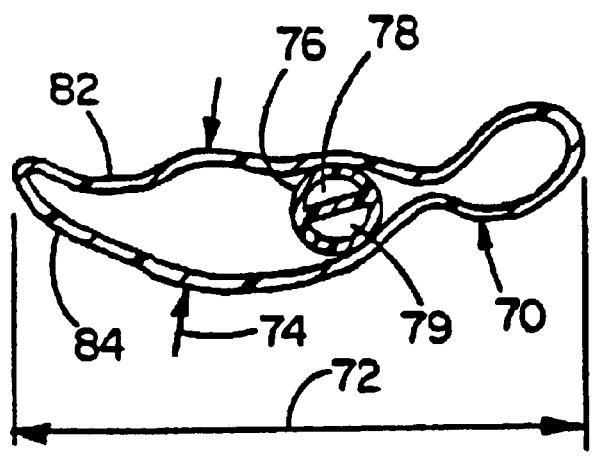
FIG. 7 describes a transverse cross section taken at the center of the length of a flattened, deflated angioplasty balloon which describes how the compaction efficiency ratio of the deflated balloon is determined.

The following examples describe in detail the construction of various embodiments of the balloon cover and catheter balloon of the present invention. Evaluation of these balloons is also described in comparison to conventional angioplasty and embolectomy balloons. FIG. 7 is provided as a description of the maximum dimension 72 and minimum dimension 74 (taken transversely to the longitudinal axis of the balloon) of a flattened, deflated angioplasty balloon 70 wherein the figure describes a transverse cross section of a typical flattened angioplasty balloon. The transverse cross section shown is meant to describe a typical deflated, flattened inelastic angioplasty balloon 70 having a somewhat irregular shape. Balloon 70 includes a catheter tube 76 having a guidewire lumen 78 and a balloon inflation lumen 79 and two opposing sides 82 and 84 of balloon 70. Maximum dimension 72 may be considered to be the maximum width of the flattened balloon 70 while minimum dimension 74 may be considered to be the maximum thickness across the two opposing sides 82 and 84 of the flattened balloon 70. All balloon and catheter measurements are expressed in terms of dimensions even if the shape is substantially circular.

EXAMPLE 1

This example illustrates the use of a balloon cover of the present invention over a commercially available angioplasty balloon. The balloon cover provides a means of returning the angioplasty balloon close to its original compact geometry after inflation and subsequent deflation, as well as providing the known chemical inertness and low coefficient of friction afforded by PTFE.

The balloon used was a MATCH 35® Percutaneous Transluminal Angioplasty (PTA) Catheter model number B508-412, manufactured by SCHNEIDER (Minneapolis, Minn.). This balloon when measured immediately after being removed from the protective sheath provided by the manufacturer had a minimum dimension of 2.04 mm and a maximum dimension of 2.42 mm. These measurements were taken from approximately the center of the balloon, as defined by the midpoint between the circumferentially-oriented radiopaque marker bands located at both ends of the balloon. A Lasermike model 183, manufactured by Lasermike, (Dayton, Ohio) was used to make the measurements while the balloon was rotated about its longitudinal axis. The shaft onto which the balloon was attached had a minimum dimension of 1.74 mm and a maximum dimension of 1.77 mm measured adjacent to the point of balloon attachment closest to the center of the length of the shaft. The balloon, when inflated to 8 atmospheres internal water pressure, had a minimum dimension of 8.23 mm and a maximum dimension of 8.25 mm at the center of the length of the balloon. When deflated by removing the entire volume of water introduced during the 8 atmosphere pressurization, the balloon at its mid-length, had a minimum dimension of 1.75 mm, and a maximum dimension of 11.52 mm as measured using Mitutoyo digital caliper model CD-6"P. Upon completion of the measurements the balloon portion of the PTA catheter was carefully repackaged into the protective sheath.

The inventive balloon cover was made from a length of porous PTFE film made as described above cut to a width of 2.5 cm. The film thickness was approximately 0.02 mm, the density was 0.2 g/cc, and the fibril length was approximately 70 microns. Thickness was measured using a Mitutoyo snap gauge model 2804-10 and density was calculated based on sample dimensions and mass. Fibril length of the porous PTFE films used to construct the examples was estimated from scanning electron photomicrographs of an exterior surface of film samples.

This film was helically wrapped onto the bare surface of an 8 mm diameter stainless steel mandrel at an angle of approximately 70° with respect to the longitudinal axis of the mandrel so that about 5 overlapping layers of film cover the mandrel. Following this, another 5 layers of the same film were helically wrapped over the first 5 layers at the same pitch angle with respect to the longitudinal axis, but in the opposite direction. The second 5 layers were therefore also oriented at an approximate angle of 70°, but measured from the opposite end of the axis in comparison to the first 5 layers. Following this, another 5 layers of the same film were helically wrapped over the first and second 5 layers at the same bias angle with respect to the longitudinal axis as the first 5 layers, and then another 5 layers of the same film were helically wrapped over the first, second, and third 5 layers at the same bias angle with respect to the longitudinal axis as the second 5 layers. This resulted in a total of about 20 layers of helically wrapped film covering the mandrel.

The film-wrapped mandrel was then placed into an air convection oven set at 380° C. for 10 minutes to heat bond the layers of film, then removed and allowed to cool. The resulting 8 mm inside diameter film tube formed from the helically wrapped layers was then removed from the mandrel and one end was ligated onto a self-sealing injection site (Injection Site with Luer Lock manufactured by Baxter Healthcare Corporation, Deerfield, Ill.). A hole was created through the injection site, and the balloon end of the previously measured PTA catheter was passed through this hole, coaxially fitting the film tube over the balloon portion as well as a portion of the shaft of the PTA catheter. The film tube was approximately 25 cm in length. With the film tube over the PTA catheter and attached to the injection site, tension was applied manually to the free end of the film tube while the injection site was held fixed, causing the film tube to reduce in diameter and fit snugly onto the underlying segment of PTA catheter. Next, the film tube was ligated at the distal end of the PTA catheter shaft so that the balloon cover remained taut and snugly fit.

At this point the now covered balloon was measured in a deflated state. The minimum dimension was found to be 2.33 mm and the maximum dimension 2.63 mm. As before, these measurements were taken from approximately the center of the balloon, as defined by the midpoint between the radiopaque marker bands, and a Lasermike model 183, manufactured by Lasermike, (Dayton, Ohio.) was used to make the measurements. The balloon, when inflated to 8 atmospheres internal water pressure had a minimum dimension of 7.93 mm and a maximum dimension of 8.06 mm at the center of the balloon. When deflated by removing the entire volume of water introduced during the 8 atmosphere pressurization, the balloon at its mid-length, had a minimum dimension of 1.92 mm and a maximum dimension of 11.17 mm. Next, tension was manually applied to the injection site causing the balloon cover to reduce the size of the underlying balloon, particularly along the plane of the 11.17 mm measurement taken previously. After the application of tension the covered balloon was measured again, and the minimum and maximum dimensions were found as 3.43 and 3.87 mm respectively.

This example shows that the balloon cover can be used effectively to compact a PTA balloon which was inflated and subsequently deflated to approximately the geometry of the balloon in an unused state. The measurements taken on the balloon (in both the uncovered and covered states) after inflation and subsequent deflation show that rather than undergoing a uniform circular compaction, the balloon tended to flatten. This flattening can be quantified by calculating the ratio of the minimum dimension to the maximum dimension measured after inflation and subsequent deflation. This ratio is defined as the compaction efficiency ratio. Note that a circular cross section yields a compaction efficiency ratio of unity. For this example, the uncovered balloon had a compaction efficiency ratio of 1.75 divided by 11.52, or 0.15. The balloon, after being provided with the inventive balloon cover, had a compaction efficiency ratio of 3.43 divided by 3.87, or 0.89. Additionally, the ratio of the maximum dimension prior to any inflation, to the maximum dimension after inflation and subsequent deflation, is defined as the compaction ratio. A balloon which has the same maximum dimension prior to any inflation, and after inflation and subsequent deflation, has a compaction ratio of unity. For this example, the uncovered balloon had a compaction ratio of 2.42 divided by 11.52, or 0.21. The balloon, after being provided with the inventive balloon cover, had a compaction ratio of 2.63 divided by 3.87, or 0.68.

EXAMPLE 2

This example illustrates the use of a balloon cover over a commercially available latex embolectomy balloon. The balloon cover provides a defined limit to the growth of the embolectomy balloon, a substantial increase in burst strength, and the known chemical inertness and low coefficient of friction afforded by PTFE.

The balloon used was a Fogarty® Thru-Lumen Embolectomy Catheter model 12TL0805F manufactured by Baxter Healthcare Corporation (Irvine, Calif.). This natural rubber latex balloon when measured immediately after being removed from the protective sheath provided by the manufacturer had a minimum dimension of 1.98 mm and a maximum dimension of 2.02 mm. These measurements were taken from approximately the center of the balloon, as defined by the midpoint between the radiopaque marker bands. A Lasermike model 183, manufactured by Lasermike, (Dayton, Ohio) was used to make the measurements while the balloon was rotated about its longitudinal axis. The shaft onto which the balloon was attached had a minimum dimension of 1.64 mm and a maximum dimension of 1.68 mm measured adjacent to the point of balloon attachment closest to the center of the length of the shaft. The balloon, when filled with 0.8 cubic centimeters of water had a minimum dimension of 10.71 mm and a maximum dimension of 10.77 mm at the center of the balloon. When deflated by removing the entire volume of water introduced, the balloon at its mid-length, had a minimum dimension of 1.97 mm and a maximum dimension of 2.04 mm. The balloon when tested using a hand-held inflation syringe had a burst strength of 60 psi.

Another embolectomy catheter of the same type was covered using a porous PTFE film tube made as described in Example 1. The method used to cover the embolectomy catheter was the same as that used to cover the PTA catheter in Example 1.

At this point, the now covered balloon was measured in a pre-inflated state. The minimum dimension was found to be 2.20 mm and the maximum dimension 2.27 mm. As before, these measurements were taken from approximately the center of the balloon, as defined by the midpoint between the radiopaque marker bands, and a Lasermike model 183, manufactured by Lasermike (Dayton, Ohio) was used to make the measurements. The balloon, when filled with 0.8 cubic centimeters of water had a minimum dimension of 8.29 mm and a maximum dimension of 8.34 mm at mid-length. When deflated by removing the entire volume of water introduced, the balloon at its mid-length, had a minimum dimension of 3.15 mm and a maximum dimension of 3.91 mm. Next, tension was manually applied to the injection site causing the balloon cover to reduce in size. After the application of tension the covered balloon was measured again, and the minimum and maximum dimensions were found as 2.95 and 3.07 mm respectively. The covered balloon was determined to have a burst strength of 188 psi, failing solely due the burst of the underlying embolectomy balloon. The inventive balloon cover exhibited no indication of rupture.

This example shows that the inventive balloon cover effectively provides a limit to the growth, and a substantial increase in the burst strength of an embolectomy balloon. The measurements taken on the uncovered balloon show that when filled with 0.8 cubic centimeters of water the balloon reached a maximum dimension of 10.77 mm. Under the same test conditions, the covered balloon reached a maximum dimension of 8.34 mm. The burst strength of the uncovered balloon was 60 psi while the burst strength of the covered balloon was 188 psi when inflated until rupture using a hand-operated liquid-filled syringe. This represents more than a three fold increase in burst strength.

EXAMPLE 3

This example illustrates the use of a composite material in a balloon application. A balloon made from the composite material described below exhibits a predictable inflated diameter, high strength, exceptional compaction ratio and compaction efficiency ratio, as well as the known chemical inertness and low coefficient of friction afforded by PTFE.

A length of SILASTIC®Rx50 Silicone Tubing manufactured by Dow Corning Corporation (Midland, Mich.) having an inner diameter of 1.5 mm and an outer diameter of 2.0 mm was fitted coaxially over a 1.1 mm stainless steel mandrel and secured at both ends. The silicone tubing was coated with a thin layer of Translucent RTV 108 Silicone Rubber Adhesive Sealant manufactured by General Electric Company (Waterford, N.Y.). An 8 mm inner diameter film tube made in the same manner described in Example 1 was fitted coaxially over the stainless steel mandrel and the silicone tubing. Tension was manually applied to the ends of the film tube causing it to reduce in diameter and fit snugly onto the underlying segment of silicone tubing secured to the stainless steel mandrel. With the film tube in substantial contact with the silicone tubing, this composite tube was gently massaged to ensure that no voids were present between the silicone tube and the porous PTFE film tube. Next the entire silicone-PTFE composite tube was allowed to cure in an air convection oven set at 35° C. for a minimum of 12 hours. Once cured, the composite tube was removed from the stainless steel mandrel. One end of the composite tube was then fitted coaxially over a section of 5Fr catheter shaft taken from a model B507-412 MATCH 35® Percutaneous Transluminal Angioplasty (PTA) Catheter, manufactured by SCHNEIDER (Minneapolis, Minn.) and clamped to the catheter shaft using a model 03.3 RER Ear Clamp manufactured by Oetiker (Livingston, N.J.) such that a watertight seal was present. The distal end of the balloon was closed using hemostats for expediency, however, a conventional ligature such as waxed thread may be used to provide a suitable closure. In this manner a balloon catheter was fashioned, utilizing the silicone-PTFE composite tube as the balloon material.

At this point, the balloon was measured in a pre-inflated state. The minimum dimension was found to be 2.31 mm and the maximum dimension 2.42 mm. As before, these measurements were taken from approximately the midpoint of the balloon, and a Lasermike model 183, manufactured by Lasermike, (Dayton, Ohio) was used to make the measurements while the balloon was rotated about its longitudinal axis. The balloon, when inflated to 8 atmospheres internal water pressure, had a minimum dimension of 7.64 mm and a maximum dimension of 7.76 mm at the center of the balloon. When deflated by removing the entire volume of water introduced during the 8 atmosphere pressurization, the balloon at its mid-length, had a minimum dimension of 2.39 mm and a maximum dimension of 2.57 mm. The silicone-PTFE composite balloon when tested using a hand-held inflation device had a burst strength of 150 psi, reaching a maximum dimension of about 7.9 mm prior to rupture.

This example illustrates that the balloon made from the silicone-PTFE composite tube exhibited a predictable limit to its diametrical growth as demonstrated by the destructive burst strength test wherein the balloon did not exceed the 8 mm diameter of the porous PTFE film tube component. The compaction ratio as previously defined was 2.42 divided by 2.57, or 0.94, and the compaction efficiency ratio as previously defined was 2.39 divided by 2.57, or 0.93.

EXAMPLE 4

This example describes the construction of a PTA balloon made by helically wrapping a porous PTFE film having a non-porous FEP coating over a thin porous PTFE tube.

The FEP-coated porous expanded PTFE film was made by a process which comprises the steps of:

a) contacting a porous PTFE film with another layer which is preferably a film of FEP or alternatively of another thermoplastic polymer;

b) heating the composition obtained in step a) to a temperature above the melting point of the thermoplastic polymer;

c) stretching the heated composition of step b) while maintaining the temperature above the melting point of the thermoplastic polymer; and d) cooling the product of step c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

The FEP-coated porous PTFE film used to construct this example was a continuous (non-porous) film. The total thickness of the coated film was about 0.02 mm. The film was helically wrapped onto an 8 mm diameter stainless steel mandrel that had been coaxially covered with a porous expanded PTFE tube, made as taught by U.S. Pat. Nos. 3,953,566 and 4,187,390. The porous PTFE tube was a 3 mm inside diameter tube having a wall thickness of about 0.10 mm and a fibril length of about 30 microns. Fibril length is measured as taught by U.S. Pat. No. 4,972,846. The 3 mm tube had been stretched to fit snugly over the 8 mm mandrel. The FEP-coated porous PTFE film was then wrapped over the outer surface of this porous PTFE tube in the same manner as described by Example 1, with the FEP-coated side of the film placed against the porous PTFE tube surface. The wrapped mandrel was placed into an air convection set at 380° C. for 2.5 minutes, removed and allowed to cool, at which time the resulting tube was removed from the mandrel. One end of this tube was fitted coaxially over the end of a 5 Fr catheter shaft taken from a model number B507-412 PTA catheter manufactured by Schneider (Minneapolis, Minn.), and clamped to the catheter shaft using a model 03.3 RER Ear Clamp manufactured by Oetiker (Livingston, N.J.) such that a watertight seal was present. The resulting balloon was packed into the protective sheath which was provided by Schneider as part of the packaged balloon catheter assembly. The balloon was then removed from the protective sheath by sliding the sheath proximally off of the balloon and over the catheter shaft. Prior to inflation, the minimum and maximum diameters of the balloon were determined to be 2.25 and 2.61 mm. The distal end of the balloon was then closed using hemostats for expediency, however, a conventional ligature such as waxed thread could have been used to provide a suitable closure. When inflated to a pressure of 6 atmospheres, the minimum and maximum diameters were 8.43 and 8.49 mm. After being deflated the minimum and maximum diameters were 1.19 and 12.27 mm. These diameters resulted in a compaction ratio of 0.21 and a compaction efficiency of 0.10.

EXAMPLE 5

This example describes a balloon constructed by impregnating silicone dispersion into a porous PTFE tube with helically applied porous PTFE film. A balloon made in this way exhibits a very small initial diameter, predictable inflated diameter, high strength, exceptional compaction ratio and compaction efficiency ratio, as well as the known chemical inertness and low coefficient of friction afforded by PTFE. The impregnation with silicone dispersion enables the construction of a thinner balloon. The use of a thin porous PTFE tube as a substrate provides longitudinal strength to resist elongation of the balloon at high pressures.

A longitudinally extruded and expanded porous PTFE substrate tube was obtained. The substrate tube was 1.5 mm inside diameter, having a wall thickness of about 0.17 mm and a fibril length of about 45 microns. The tube was fitted coaxially onto a 1.5 mm diameter stainless steel mandrel. Next, a length of porous expanded PTFE film was obtained that had been cut to a width of 2.54 cm. This film had a thickness of about 0.02 mm, a density of about 0.2 g/cc, and a fibril length of about 70 microns. Thickness was measured using a Mitutoyo snap gauge model No. 2804-10. The film bulk density was calculated based on dimensions and mass of a film sample. Density of non-porous PTFE was considered to be 2.2 g/cc. Fibril length of the porous PTFE film used to construct the example was estimated from scanning electron photomicrographs of an exterior surface of samples of the film.

This film was helically wrapped directly onto the bare metal surface of a 7 mm diameter stainless steel mandrel at about 65° with respect to the longitudinal axis of the mandrel so that about two overlapping layers of film covered the mandrel. Both edges of the film were colored with black ink in order to measure the pitch angles of the film during the construction or use of the completed balloon. Following this, another approximately two layers of the same film were helically wrapped over the first two layers. The second two layers were applied at the same bias angle with respect to the longitudinal axis, but in the opposite direction. This procedure was repeated three times, providing approximately 16 total layers of film. The film-wrapped mandrel was then placed into a convection oven set at 380° C. for 10 minutes to heat-bond the adjacent layers of film, then removed and allowed to cool. The resulting 7 mm inside diameter film tube formed from the helically wrapped layers of films was then removed from the mandrel.

This 7 mm inside diameter porous PTFE film tube was then fitted coaxially over the 1.5 mm inside diameter PTFE substrate tube and mandrel. The film tube was then tensioned longitudinally to cause it to reduce in diameter to the extent that it fit snugly over the outer surface of the 1.5 mm tube. The ends of this reinforced tube were then secured to the mandrel in order to prevent longitudinal shrinkage during heating. The combined tube and mandrel assembly was placed into an air convention oven set at 380° C. for 190 seconds to heat bond the film tube to the outer surface of the substrate tube. The reinforced tube and mandrel assembly was then removed from the oven and allowed to cool.

Additional porous PTFE film was then helically applied to outer surface of the reinforced tube to inhibit wrinkling of the tube in the subsequent step. The tube was then compressed in the longitudinal direction to reduce the tube length to approximately 0.6 of the length just prior to this compression step. Care was taken to ensure a high degree of uniformity of compression along the length of the tube. Wire was used to temporarily affix the ends of the tube to the mandrel. The mandrel-loaded reinforced tube with the additional helically applied film covering was then placed into a convention oven set at 380° C. for 28 seconds, removed from the oven and allowed cool.

The additional outer film was removed from the reinforced tube, followed by removing the reinforced tube from the mandrel. The reinforced tube was then gently elongated by hand to a length of about 0.8 of the length just prior to the compression step.

The reinforced tube was then ready for impregnation with silicone dispersion (Medical Implant Grade Dimethyl Silicone Elastomer Dispersion in Xylene, Applied Silicone Corp., PN 40000, Ventura, Calif.). The silicone dispersion was first prepared by mixing 2.3 parts n-Heptane (J. T. Barker, lot #J07280) with one part silicone dispersion. Another mixture with n-Heptane was prepared by mixing 0.5 parts with 1 part silicone dispersion. Each mixture was loaded into an injection syringe.

The dispensing needle of each of the injection syringes was inserted inside one end of the reinforced tube. Wire was used to secure the tube around the needles. One of the dispensing needles was capped and the syringe containing the 2.3:1 silicone dispersion solution was connected to the other. The solution was dispensed inside the reinforced tube with about 6 psi pressure. Pressure was maintained for approximately one minute, until the outer surface of the tube started to become wetted with the solution, indicating that the dispersion entered the pores of the PTFE material. It was ensured that the silicone dispersion coated the inside of the PTFE tube. At this point, the syringe was removed, the cap was removed from the other needle, and the syringe containing the 0.5:1 silicone dispersion solution was connected to the previously-capped needle. This higher viscosity dispersion was then introduced into the tube with the syringe, displacing the lower viscocity dispersion through the needle at the other end, until the higher viscosity dispersion began to exit the tube through the needle. After ensuring that the tube was completely filled with dispersion, both needles were capped. Curing of the silicone dispersion was effected by heating the assembly in a convection oven set at 150° C. for a minimum of one hour. The solvent evaporated during the curing process, thereby recreating the lumen in the tube. The impregnated reinforced tube was removed from the oven and allowed to cool. Both ends of the tube were opened and the 0.5:1 silicone dispersion solution was injected in one end to again fill the lumen, the needle ends were then capped, then the dispersion was cured in the same manner as described above. At this point the balloon construction was complete.

The above-described process preserved PTFE as the outermost surface of the balloon. Alternatively, longer impregnation times or higher injection pressures during the initial impregnation could cause more thorough wetting of the PTFE structure with the silicone dispersion, thereby driving more dispersion to the outermost surface of the balloon.

Figure 8:
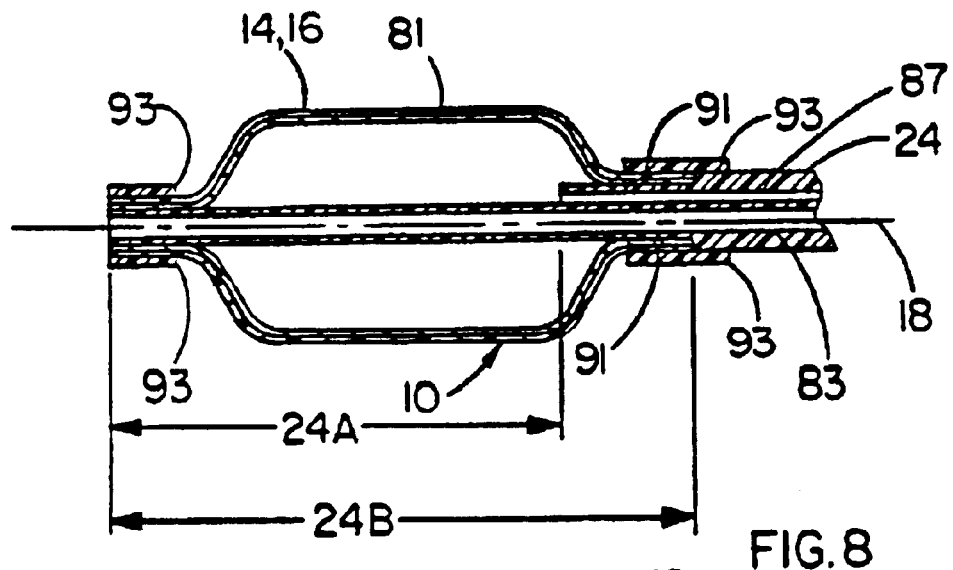
FIG. 8 describes a longitudinal cross section of a balloon affixed to the shaft of a dual lumen catheter, the balloon having a first PTFE material oriented substantially parallel to the longitudinal axis of the balloon and a second PTFE material oriented substantially circumferential to the longitudinal axis, wherein the PTFE materials is impregnated with an elastomer.
Figure 8A:
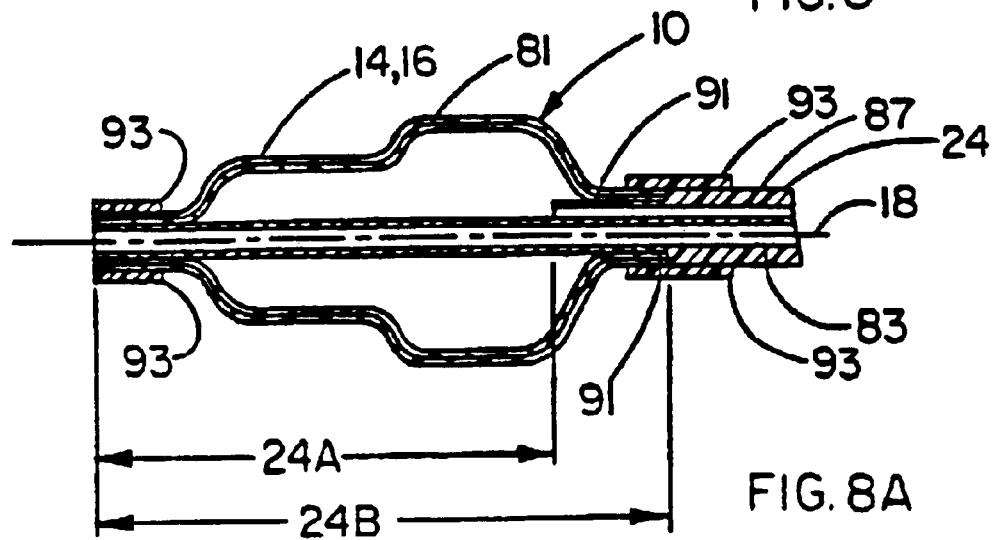
FIG. 8A describes a longitudinal cross section of an alternative embodiment to that of FIG. 8 wherein the balloon during inflation exhibits a larger diameter at a first portion of its length than at a second portion of its length.

The balloon was then ready for mounting on a 5 Fr catheter shaft obtained from a balloon dilatation catheter (Schneider Match 35 PTA Catheter, 6 mm dia., 4 cm length, model no. B506-412) This balloon was mounted on the 1.67 mm diameter catheter shaft as described by FIG. 8. Both ends of the balloon were mounted to the shaft. The catheter tip portion plus the balloon of the balloon dilatation catheter were cut off in the dual lumen portion of the shaft leaving only the catheter shaft 24. Guidewires serving as mandrels (not shown) were inserted into both lumens of the shaft. A 0.32 mm mandrel was inserted into the inflation lumen 87 and a 0.6 mm mandrel was inserted into the wire lumen 83. The portion 24A of the shaft 24 containing the inflation lumen 87 was shaved off longitudinally to a length approximately 1 cm longer than the length of the balloon to be placed on the shaft; therefore, this portion 24A of the shaft 24 then contained only the wire lumen 83 which possessed a semi-circular exterior transverse cross section. (The extra 1 cm length accommodates room for a tip portion of the catheter, without a balloon covering, in the final assembly.) With the mandrels still in place, portion 24B of the shaft 24 was inserted for about 30 seconds into a heated split die containing 1.5 mm diameter bore when the dies were placed together. The dies were heated to a temperature of 180° C. to form the semicircular cross sectional shape of the portion of the shaft into a round 1.5 mm cross section and to create a landing 91 in the area proximal to the distal end of the inflation lumen 87. Next, the balloon 10 (having circumferentially oriented film layers 14 and 16, and longitudinally oriented substrate tube 81) was slipped over the modified distal end of the shaft 24 such that the proximal end of the balloon 10 was approximately 0.5 cm from the end of the landing 91. This approximately 0.5 cm segment of the landing 91 adjacent to the abutment was primed for fifteen seconds (Loctite Prism™ Primer 770, Item #18397, Newington, Conn.) and then cyanoacrylate glue (Loctite 4014 Instant Adhesive, Part #18014, Rocky Hill, Conn.) was applied to that segment. The balloon 10 was moved proximally such that the proximal end of the balloon abutted against the end of the landing 91 and the glue was allowed to set. The distal end of the balloon 10 was attached in the same manner, while ensuring against wrinkling of the balloon during the attachment. At this point, a radiopaque marker could have been fitted at each end of the balloon. The last step in the mounting process involved securing the ends of the balloon with shrink tubing 93 (Advanced Polymers, Inc., Salem, N.H., polyester shrink tubing—clear, item #085100CST). Approximately 0.25 cm of the proximal end of the balloon and approximately 0.75 cm of the shaft adjacent to the end of the balloon were treated with the same primer and glue as described above. Approximately 1 cm length of shrink tubing 93 was placed over the treated regions of the shaft 24 and balloon 10. The same process was followed to both prepare the distal end the balloon and the adjacent modified shaft portion and to attach another approximately 1 cm length of shrink tubing 93. The entire assembly was then placed into a convection oven set at 150° C. for at least about 2 minutes in order to shrink the shrink tubing.

The pre-inflation balloon possessed 2.03 mm and 2.06 mm minimum and maximum dimensions, respectively. the balloon catheter was tested under pressure as described in Example 1. The inflated balloon possessed 5.29 mm and 5.36 mm minimum and maximum dimensions, respectively. The deflated balloon possessed 2.19 mm and 3.21 mm minimum and maximum dimensions, respectively. The resulting compaction efficiency and the compaction ratio were 0.68 and 0.64, respectively.

The pitch angles of the film were also measured pre-inflation, at inflation (8 atm), and at deflation, yielding values of about 20°, 50°, and 25°, respectively. The balloon was reinflated with 10 atm and the pitch angles of the film were measured for the inflation and deflation conditions. The angles were the same for both inflation pressures.

The balloon was subjected to even higher pressures to determine the pressure at failure. The balloon withstood 19.5 atm pressure prior to failure due to breakage of the shrink tubing at the distal end of the balloon. Another balloon catheter was made using a piece of the same balloon material, following the same procedures described in this example. This balloon catheter was used to distend a 3 mm GORE-TEX Vascular Graft (item no. V03050L, W. L. Gore and Associates, Inc., Flagstaff Ariz.) from which the outer reinforcing film had been removed. The graft was placed over the balloon such that the distal end of the graft was positioned approximately 1 cm from the distal end of the balloon. The balloon was inflated to 8 atm, the graft distended uniformly without moving in the longitudinal direction with respect to the balloon. Another piece of the same graft was tested in the same manner using a 6 mm diameter, 4 cm long Schneider Match 35 PTA Catheter (model no. B506-412). In this case, the graft slid along the length of the balloon proximally during the balloon inflation; the distal end of the graft was not distended.

EXAMPLE 6

A balloon catheter was made following all of the steps of Example 5 with one exception in order to provide a balloon that bends during inflation.

All of the same steps were followed as in Example 5 with the exception of eliminating the manual elongation step that immediately followed the longitudinal compression step. That is, at the point of being impregnated with silicone dispersion, the film-covered porous PTFE tube was 0.6 of its initial length (instead of 0.8 as in Example 5).

A balloon catheter was constructed using this balloon. The length of the balloon was 4.0 cm. The bend of the balloon was tested by inflating the balloon to 8 atm and measuring the bend angle created by inflation. Measurements were made via the balloon aligned coincident with the 0° scribe line of a protractor, with the middle of the balloon positioned at the origin. The bend angle was 50°. The balloon was then bent an additional 90° and allowed to relax. No kinking occurred even at 140°. The angle of the still inflated, relaxed balloon stabilized at 90°.

The balloon of an intact 6 mm diameter, 4 cm long Schneider Match 35 PTA Catheter (model no. B506-412) was tested in the same manner. The bend angle under 8 atm pressure was 0°. The inflated balloon was then bent to 90°, which created a kink. The inflated balloon was allowed to relax. The balloon bend angle stabilized at 25°. The bending characteristics of an article of the present invention should enable the dilatation of a vessel and a side branch of the same vessel simultaneously. The inventive balloon is easily bendable without kinking. Kinking is defined as wrinkling of the balloon material.

EXAMPLE 7

This example illustrates an alternative construction for a balloon catheter assembly of the present invention. The described construction relates to a balloon made from tubular substrates of helically-wrapped porous PTFE film and elastomeric tubing in laminar relationship wherein ends of the balloon are secured to a catheter shaft using wraps of porous PTFE film. The balloon does not require an additional layer of porous PTFE having fibrils oriented longitudinally with respect to the lengths of the balloon and catheter shaft.

Figure 9:
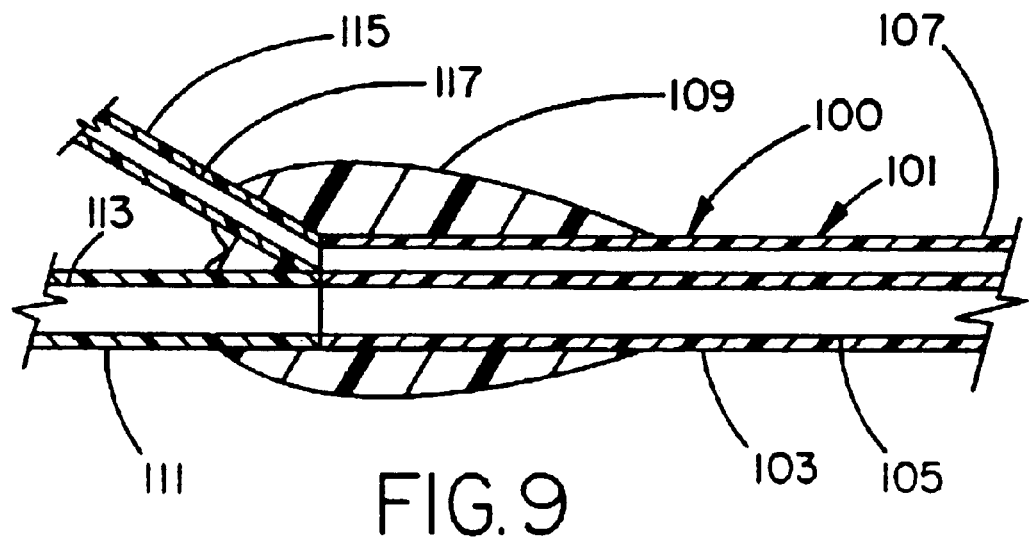
FIGS. 9 and 9A describe cross sections of the proximal end of a balloon catheter of the present invention.
Figure 9A:
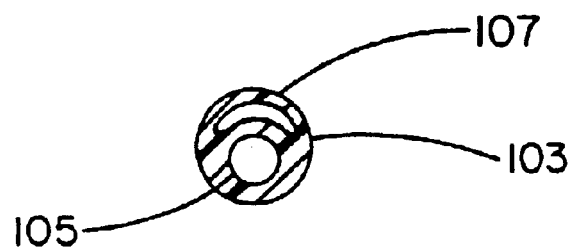

As shown by the longitudinal cross section of FIG. 9, the proximal end of the balloon catheter assembly 100 was created using three segments of catheter tubing joined together at an injection molded Y-fitting. As described in this and subsequent examples, the distal end of the balloon catheter is considered to be the end to which is affixed the balloon and the end which is first inserted into the body of a patient; the proximal end is considered to be the end of the balloon catheter opposite the distal end. All tubing segments were Pebax 7233 tubing unless noted otherwise; all of the described tubing is available from Infinity Extrusions and Engineering, Santa Clara, Calif. unless noted otherwise. The primary component of catheter shaft 101 was a dual lumen segment of tubing 103 having an outside diameter of about 2.3 mm, a guidewire lumen 105 of about 1.07 mm inside diameter and a crescent-shaped inflation lumen 107 of about 0.5 mm height. A transverse cross section of this tubing is described by FIG. 9A. The guidewire lumen 105 of this main shaft 101 was joined at the Y-fitting 109 to one end of a 12 cm length of single lumen tubing 111 having an outside diameter of about 2.34 mm and an inside diameter of about 1.07 mm; the inflation lumen 107 of the main shaft 101 was joined to a 12 cm length of Pebax 4033 single lumen tubing 115. Joining was accomplished by placing a length of 1.0 mm outside diameter steel wire (not shown) into one end of the guidewire lumen 105 of the dual lumen tubing 103 and sliding one end of single lumen tube 111 onto the opposite end of the steel wire until the ends of dual lumen tube 103 and single lumen tube 111 abutted. A length of 0.48 mm diameter wire (also not shown) having a 30° degree bend at the midpoint of its length was inserted into the crescent-shaped inflation lumen 107 of the dual lumen tubing 103 up to the point of the bend in the wire; the lumen 117 of the second length of single lumen tubing 115 was fitted over the opposite end of this wire until it also reached the bend point of the wire, abutting the end of the dual lumen tubing 103 at that point. The presence of the wires in the region of the abutted tube ends thus maintained the continuity of both lumens at the point of abutment. The region of the abutted tubing ends was placed into the cavity of a mold designed to encapsulate the junction. Using a model IMP 6000 Injection Molding Press (Novel Biomedical Inc., Plymouth Minn.), heated Pebax 7033 was injected into the mold to form Y-fitting 109. After cooling, the resulting assembly was removed from the mold and the lengths of steel wire were withdrawn from the lumens of the tubing. Finally, a female Luer fitting (part no. 65250, Qosina Corp., Edgewood, N.Y.) was affixed to the remaining ends of each of the single lumen tubes 111 and 115 using Loctite 4014 Instant Adhesive (Loctite Corp., Newington Conn.).

Figure 10A:
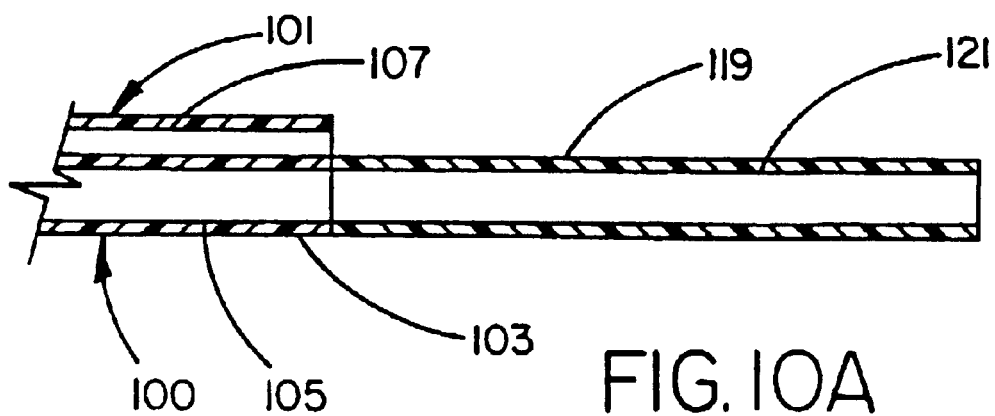

The distal or balloon end of the catheter assembly 100 was then fabricated as follows, beginning according to the longitudinal cross section shown by FIG. 10A. A 1.00 mm diameter stainless steel wire (not shown) approximately 30 cm long was inserted approximately 15 cm into the distal end of the guidewire lumen 105 of the dual lumen tubing 103. A 13 cm length of single lumen tubing 119 having an inner diameter of 1.02 mm and an outer diameter of 1.58 mm was placed over the exposed wire protruding from the guidewire lumen 105 such that it abutted the end of the dual lumen tubing 103. A 0.49 mm stainless steel wire approximately 30 cm long was placed inside the distal end of the crescent-shaped inflation lumen 107 of the dual lumen tubing 103. The abutted ends of the two tubes 103 and 119 and the resident wires were placed into a PIRF® Thermoplastic Forming and Welding System (part numbers 3220, 3226, 3262 and 3263, Sebra® Engineering and Research Associates, Inc., Tucson Ariz.) and a butt connection between the single lumen tubing 119 and the dual lumen catheter shaft 103 was completed. The 0.49 mm stainless steel wire resident within the distal portion of the crescent-shaped inflation lumen 107 of the dual lumen catheter tubing 103 ensured that the distal end of lumen 107 would remain open during this operation. The heated die used in this step was specifically fabricated to accommodate the dimensions of the dual lumen catheter tubing 103 and the single lumen tubing 119. The heating and other parameters used in the operation were derived by trial and error to result in adequate reflow and butt welding of the abutted ends of the two tubes.

Figure 10B:
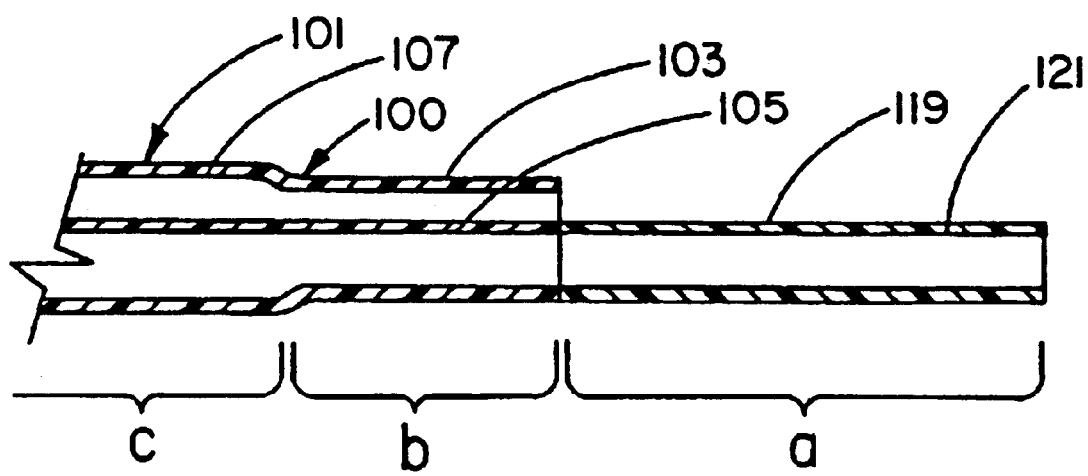

Next, with the 1.00 mm stainless steel wire still in place within the guidewire lumens 105 and 121 of abutted tubes 103 and 119, the 0.49 mm stainless steel wire resident within the distal portion of the inflation lumen 107 of the dual lumen catheter tubing 103 was replaced by a 0.39 mm stainless steel wire approximately 30 cm long (also not shown). Again the wire was placed about 15 cm into the inflation lumen 107. The assembly consisting of butt welded single lumen tube 119 and dual lumen tube 103, and the resident wire, was placed into the PIRF® Thermoplastic Forming and Welding System which was refitted with a different die. Upon heating, the assembly was advanced approximately 2.0 cm into the heated die of the system, causing a 2 cm length of the distal end of the outer diameter of the dual lumen catheter tubing 103 to decrease to the same dimension as the 1.83 mm inner diameter of the heated die. The longitudinal cross section of FIG. 10B describes the appearance of the assembly after heating wherein region "a" has the 1.58 mm outside diameter of single lumen tube 119, region "b" has been modified to the outside diameter of 1.83 mm and region "c" retains the original 2.3 mm outside diameter of dual lumen tubing 103. The 0.39 mm stainless steel wire resident within the inflation lumen 107 of the dual lumen catheter tubing 103 ensured that the lumen 107 would remain open during this operation. The heating and other parameters used in the operation were derived by trial and error to result in adequate reflow of the dual lumen tubing. Once this operation was completed, the entire outer surface of the full length of the single lumen tubing 119 (region "a," distal from the butt-weld) was abraded with 220 abrasive paper to facilitate bonding of the ends of a silicone tube 123 as will be described.

Figure 10C:
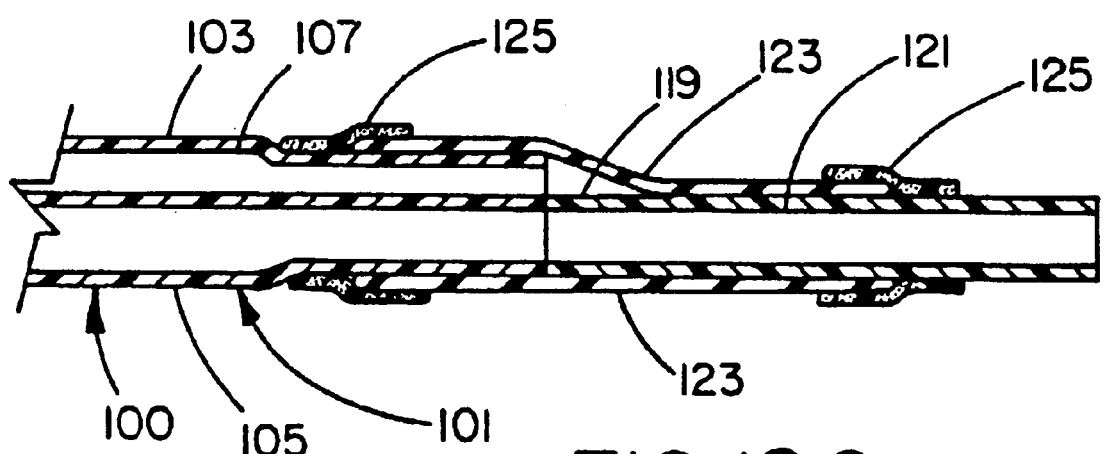

With construction of the catheter shaft 101 completed, a segment of silicone tubing 123 approximately 9 cm in length, having an approximate inner diameter of 1.40 mm, an approximate outer diameter of 1.71 mm, and a durometer of Shore 60A (Beere Precision Silicone, Racine, Wis.) was placed over the distal end of the catheter shaft 101 as shown by the longitudinal cross section of FIG. 10C such that the proximal edge of the silicone tubing 123 was approximately 7.5 mm distal from the point at which the outer diameter of catheter shaft 101 changed from 1.83 mm to 2.3 mm. This was done very carefully to ensure that no section of the silicone tubing 123 was longitudinally stretched (i.e., under tension) when at its final position on the catheter shaft 101. Isopropyl alcohol was used as a lubricant between the catheter shaft 101 and the silicone tubing 123.

While the elastomeric tubing used for this example was silicone tubing, it is believed that tubings made from other elastomeric materials such as polyurethane or fluoroelastomer tubings may also be suitably employed.

With the silicone tubing 123 placed correctly on the catheter shaft 101, any residual alcohol was allowed to evaporate for a generous amount of time, ensuring that the shaft 101 was completely dry. Once free of residual alcohol, a small amount of Medical Implant Grade Dimethyl Silicone Elastomer Dispersion In Xylene (Part 40000, Applied Silicone, Ventura, Calif.) was applied between the ends of the silicone tubing 123 and the underlying exterior surface of the catheter shaft 101. At each end of the silicone tubing 123, a small blunt needle was inserted between the ends of the silicone tubing 123 and the underlying catheter shaft 101 for a distance of approximately 7.5 mm as measured in a direction parallel to the length of the catheter shaft 101. The silicone elastomer dispersion was carefully applied, using a 3 cc syringe connected to the blunt needle, around the entire circumference of the catheter shaft 101 such that the dispersion remained within and fully coated the 7.5 mm length of the area to be bonded under the ends of silicone tubing 123. The silicone elastomer dispersion was then allowed to cure for approximately 30 minutes at ambient temperature, and then an additional 30 minutes in an air convection oven set at 15° C. Next, a length of porous PTFE film as described above, approximately 1.0 cm wide, was manually wrapped over the end regions of the silicone tubing 123 under which the silicone elastomer dispersion was present, and onto the adjacent portions of the catheter shaft 101 not covered by silicone tubing 123, for a length of approximately 7.5 mm measured from the ends of the silicone tubing 123. During wrapping, the entire length of the porous PTFE film was coated with a small amount of the silicone elastomer dispersion, the dispersion impregnating the porous PTFE film such that the void spaces in the porous PTFE film were substantially filled by the dispersion. The dispersion was thus used as an adhesive material to affix the porous PTFE film to the underlying components. It is believed that other adhesive material may also be used such as other elastomers (e.g., polyurethane or fluoroelastomers, also optionally in dispersion form), cyanoacrylates or thermoplastic adhesives such as fluorinated ethylene propylene which may be activated by the subsequent application of heat. Great care was taken to ensure that the porous PTFE film was applied so that approximately 3 overlapping layers (depicted schematically as layers 125 in FIG. 10C) covered each of the regions; the very thin porous PTFE film did not add significantly to the outside diameter of the catheter assembly 100. At this point the silicone elastomer dispersion used to coat the porous PTFE film was allowed to cure for approximately 30 minutes at ambient temperature, and then an additional 30 minutes in an air convection oven set at 150° C.

Next, a film tube was constructed in a fashion similar to that described in example 1. A length of porous PTFE film, cut to a width of 2.5 cm, made as described above, was wrapped onto the bare surface of an 8 mm stainless steel mandrel at an angle of approximately 70° with respect to the longitudinal axis of the mandrel so that about 5 overlapping layers of film covered the mandrel (i.e., any transverse cross section of the film tube transects about five layers of film). Following this another, another 5 layers of the same film were helically wrapped over the first 5 layers at the same pitch angle with respect to the longitudinal axis, but in the opposite direction. The second 5 layers were therefore also oriented at an approximate angle of 70°, but measured from the opposite end of the axis in comparison to the first 5 layers. In the same manner, additional layers of film were applied five layers at a time with each successive group of five layers applied in an opposing direction to the previous group until a total of about 30 layers of helically wrapped film covered the mandrel. This film-wrapped mandrel was then placed into an air convection oven set at 380° C. for 11.5 minutes to heat bond the layers of film, then removed and allowed to cool.

The film tube may also be constructed using more film or less film than described above; the use of increasing or decreasing amounts of film will result in a catheter balloon that is respectively stronger (in terms of hoop strength) and less compliant, or weaker and more compliant. The use of slightly different porous PTFE materials (e.g., porosity, thickness and width), the amount of porous PTFE material used and its orientation with respect to the longitudinal axis and adjacent material layers can all be expected to affect the performance properties of the resulting balloon; these variables may be optimized for specific performance requirements by ordinary experimentation.

The resulting 8 mm inside diameter film tube was then removed from the 8 mm mandrel, fitted coaxially over a 1.76 mm diameter stainless steel mandrel, and manually tensioned longitudinally to cause it to reduce in diameter. The ends of the film tube (extending beyond the mandrel ends) were then placed into a model 4201 Tensile Testing Machine manufactured by Instron (Canton, Mass.) equipped with flat faced jaws and pulled at a constant rate of 200 mm/min until a force between 4.8 and 4.9 kg was achieved. The film tube was then secured to the mandrel ends by tying with wire.

The 1.76 mm mandrel with the film tube secured onto it was then placed into an air convection oven set at 380° C. for 30 seconds. The mandrel and film tube were then removed, allowed to cool, and then helically wrapped manually (using a pitch angle of about 70 degrees with respect to the longitudinal axis) with a length of 1.9 cm wide porous PTFE film made as described above, so that about 2 overlapping layers of film covered the mandrel and film tube. Following this, another 2 layers of the same film were helically wrapped over the first 2 layers at the same pitch angle with respect to the longitudinal axis, but in the opposite direction. These layers of film (not shown) were applied temporarily as a clamping means to secure the film tube to the outer surface of the mandrel during the subsequent heating and curing process. The 1.76 mm mandrel, with the film tube secured onto it and the layers of porous PTFE film wrapped over the film tube, was then placed into an air convection oven set at 380° C. for 45 seconds, after which it was removed and allowed to cool. Using an indelible pen, marks were then placed along the length of wrapped film tube in 1 cm increments, and the wrapped film tube was compressed longitudinally until these marks were uniformly spaced approximately 5 mm apart. These pen marks were placed on the external, helically-wrapped film such that the ink penetrated the outer film layers and also marked the underlying film tube. The 1.76 mm mandrel, with the longitudinally compressed film tube secured onto it and the layers of porous PTFE film wrapped over the film tube, was then placed into an air convection oven set at 380° C. for 45 seconds, after which it was removed and allowed to cool. Once cool, the layers of porous PTFE film wrapped over the film tube were completely removed, and the resulting 1.76 mm inside diameter film tube was removed from the mandrel. The film tube, having visible pen marks at 5 mm increments, was manually tensioned longitudinally until the pen marks were spaced at approximately 1 cm increments, and then allowed to retract. The resulting 1.76 mm inside diameter film tube then had visible pen marks spaced between 7 mm and 8 mm apart. The film tube was then placed in a jar containing a mixture of 1 part MED1137 Adhesive Silicone Type A manufactured by NuSil Silicone Technology (Carpinteria, Calif.) to 6 parts n-Heptane (J. T. Baker, Phillipsburg, N.J.) by weight, wetting the film tube with the mixture. Void spaces within the porous PTFE film tube 127 were thus impregnated with and substantially filled by the silicone adhesive mixture. It is believed that this step may also be accomplished by other types of elastomeric adhesives including fluoroelastomers and polyurethanes.

Figure 10D:
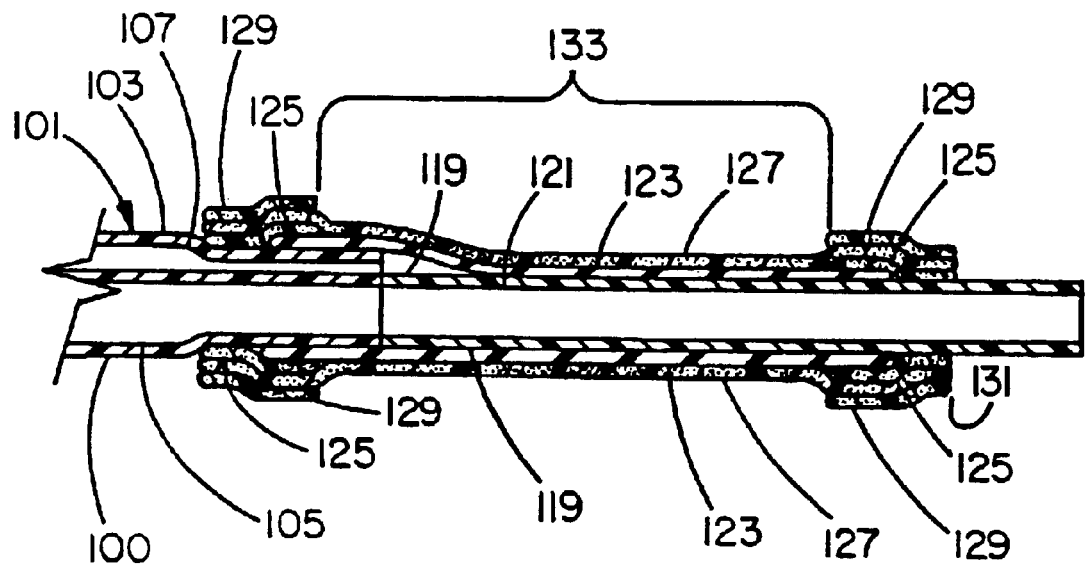

The catheter shaft 101 with the silicone tubing 123 affixed to it via porous PTFE film 125 and silicone elastomer dispersion was then carefully coated with a thin layer of a mixture of 2 parts MED1137 Adhesive Silicone Type A manufactured by NuSil Silicone Technology (Carpinteria, Calif.) to 1 part n-Heptane (J. T. Baker, Phillipsburg, N.J.) by weight. The 1.76 mm inside diameter film tube was removed from the silicone-Heptane mixture, and the coated catheter shaft 101 was carefully fitted coaxially within the film tube 127 as shown by the longitudinal cross section of FIG. 10D such that the entire silicone tube 123 affixed to the shaft 101 was covered by film tube 127, as well as an adjacent portion of the catheter shaft 101 proximal to the point at which the shaft outer dimension changed from 1.83 mm to 2.3 mm. With the catheter shaft 101 and the affixed silicone tube 123 covered by the film tube 127, the ends of film tube 127 were trimmed so that the proximal end was coincident to the point at which the catheter shaft 101 outer dimension changed from 1.83 mm to 2.3 mm, and the other end was approximately 7.5 mm distal from the distal end of the silicone tubing 123 affixed to the catheter shaft 101. The exterior surface of film tube 127 was then helically wrapped by hand with a length of 1.9 cm wide porous PTFE film, made as described above, so that about 2 overlapping layers of film covered its length. This film (not shown) was applied temporarily as a securing means desired during the subsequent heating and curing step. This distal portion of the catheter assembly 100 was then placed into a steam bath for a period of time between 15 and 30 minutes to cure the previously applied silicone adhesive mixture.

The catheter assembly 100 was then removed from the steam bath, and the outer helically-wrapped film layers were removed. Next, lengths of porous PTFE film as described above, approximately 1.0 cm wide, were manually wrapped over the ends of the film tube 127 approximately 15 mm distal from the point at which the shaft outer dimension changed from 1.83 mm to 2.3 mm, and approximately 15 mm distal from the most proximal edge of the porous PTFE film wrapped around the distal end of the silicone tubing . During wrapping, the entire length of the porous PTFE film was coated with a small amount of a mixture of equal parts of MED1137 Adhesive Silicone Type A manufactured by NuSil Silicone Technology (Carpinteria, Calif.) and n-Heptane (J. T. Baker, Phillipsburg, N.J.) by weight. Great care was taken to ensure that the porous PTFE film was applied so that approximately 3 overlapping layers (shown schematically as layers 129 in FIG. 10D) covered the region without adding significantly to the diameter of the catheter. Because of the reduced diameter at region "b" and the thin character of the porous PTFE film used for layers 129 and 125, the diameter of the catheter assembly 100 at the location of film layers 129 and 125 was very close to the diameter of catheter tubing 101 proximal to these layers of film. The distal portion of the catheter was then placed into a steam bath for a minimum of 8 hours to achieve final curing. After final curing the distal-most portion of the catheter shaft was cut off transversely at the distal-most edge 131 of the porous PTFE film on the exterior of the film tube. The construction of the distal region of the catheter assembly 100 incorporating the balloon portion was now complete. The resulting balloon portion of this construction is represented as region 133. The ends of the balloon and the length of the balloon (taken as the distance measured between the ends of the balloon) are defined by the bracketed region 133, shown as beginning at the edges of porous PTFE film layer 129 (the termination or securing means) closest to the balloon portion 133.

The balloon portion 133 thus was secured to the outer surface of the catheter shaft by two separate terminations (or securing means) at each end of the balloon; these take the form of film layers 125 used to secure the silicone tube 123 and film layers 129 used to secure the porous PTFE film tube 127. The presence of two separate terminations (i.e., separate layers 125 and 129) at one end of the balloon can be demonstrated by taking a transverse cross section through the termination region and examining it with suitable microscopy methods such as scanning electron microscopy.

The inflatable balloon portion 133 was the result of two substrates, porous PTFE film tube 127 and elastomeric silicone tube 123 being joined in laminated relationship. The void spaces of the porous PTFE film tube 127 were thus substantially sealed by the silicone tube 123 and the previously applied silicone adhesive mixture which impregnated the void spaces of the porous PTFE film tube 127 and adhered the film tube to the silicone tube 123.

Figure 10E:
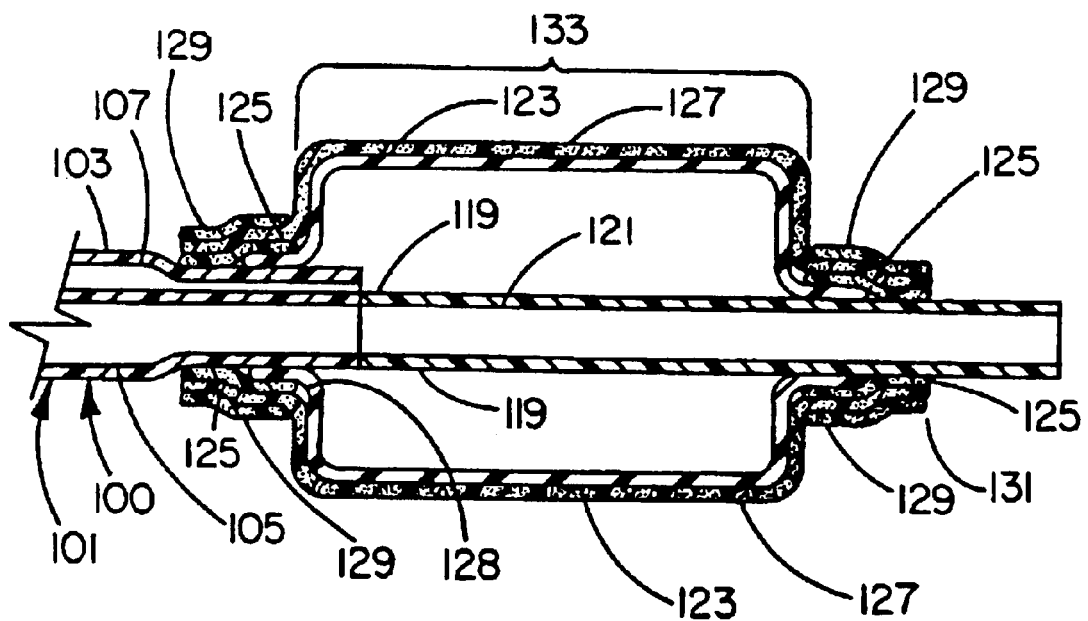

At this point, the diameter of the balloon portion 133 was measured in a pre-inflated state. The minimum diameter was found to be 2.14 mm and the maximum diameter 2.31 mm. As before, these measurements were taken from approximately the midpoint of the balloon, and a Lasermike model 183, manufactured by Lasermike, (Dayton, Ohio) was used to make the measurements while the balloon was rotated about its longitudinal axis. The balloon when inflated to 8 atmospheres internal water pressure (as described by the longitudinal cross section of FIG. 10E) for a period of 1 minute or less, had a minimum diameter of 6.89 mm and a maximum diameter of 6.93 mm at the center of its length. It was noted during the 8 atmosphere pressurization that the balloon portion 133 was substantially straight with respect to the longitudinal axis of the catheter shaft 101, and that the distance from the point at which the balloon portion 133 was attached to the catheter shaft 101 to the point on the balloon portion 133 at which the balloon was at its full diameter was relatively short. This is to say that the balloon when inflated possessed blunt ends of substantially the same diameter as the midpoint of the length of the balloon portion 133, as opposed to having a tapered appearance along the length with a smaller diameter adjacent the balloon ends. When deflated by removing the entire volume of water introduced during the 8 atmosphere pressurization, the balloon at its mid-length had a minimum diameter of 2.22 mm and a maximum diameter of 2.46 mm. This silicone-PTFE composite balloon, when tested using a hand-held inflation device, had a burst pressure of approximately 22 atmospheres (achieved beginning from zero pressure in about 30 seconds), reaching a maximum diameter of about 7.95 mm prior to failure by rupture.

This example illustrates that the balloon, constructed as described above using silicone and PTFE, exhibited a predictable limit to its diametrical growth as demonstrated by the destructive burst test wherein the balloon did not exceed the 8 mm diameter of the porous PTFE film tube component prior to failure. The compaction ratio as previously defined was 2.31 divided by 2.46, or 0.94, and the compaction efficiency ratio as previously defined was 2.22 divided by 2.46, or 0.90. The ability of the balloon to inflate to the described pressures without water leakage demonstrated effectively that the void spaces of the porous PTFE had been substantially sealed by the elastomeric material.

A flow chart describing the process used to create the balloon catheter described by this example is presented as FIG. 10F; it will be apparent that variations on this process may be used to create the same or similar balloon catheters.

EXAMPLE 8

This example teaches a method of balloon catheter construction using a catheter shaft made of elastomeric material. While this example was made using only a single lumen silicone catheter shaft with the lumen for intended for inflation, it will be apparent that a dual or multiple lumen shaft may also be used.

Figure 11A:
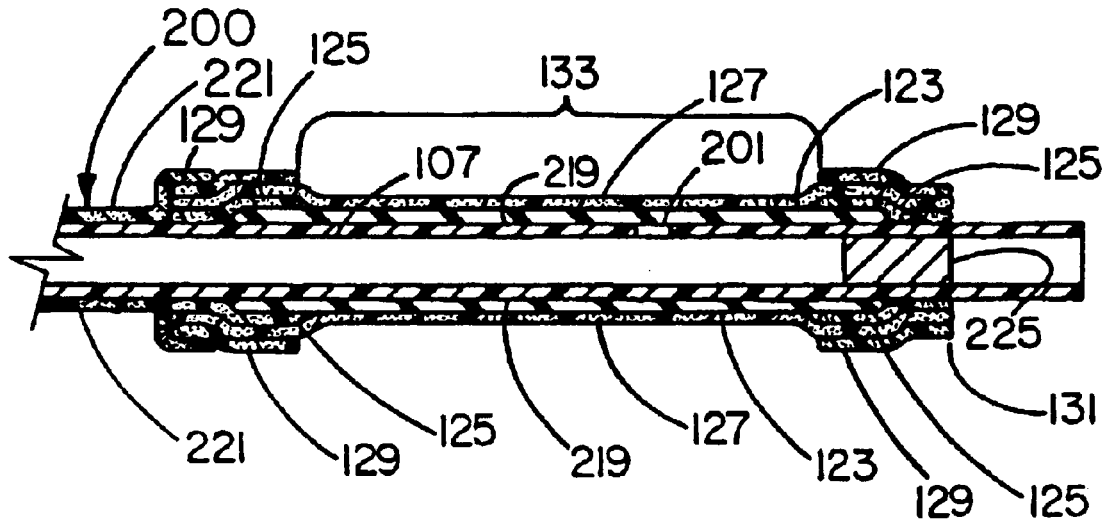

A silicone model 4 EMB 40 Arterial Embolectomy Catheter manufactured by the Cathlab Division of American Biomed Inc. (Irvine, Calif.) having a 4 fr shaft outside diameter (about 1.35 mm) and a length of 40 cm was acquired. The embolectomy catheter included a Luer fitting at the proximal end of the shaft and a balloon made of a silicone elastomer at the distal end of the shaft. The most distal 20 cm portion of the catheter (including the balloon) was cut off, and a 0.38 mm diameter wire was inserted completely through the open lumen of the shaft. A cut, approximately 5 mm in length, was made through the shaft wall approximately 6.5 cm proximal from the distal end, exposing the 0.38 mm wire but not damaging the remainder of the shaft. As shown by the longitudinal cross section of FIG. 11A, the resulting opening 201 was intended to serve as the inflation port for the new balloon which was to be constructed over this region of the catheter shaft 219.

A segment of silicone tubing 123 approximately 8 cm in length, having an approximate inner diameter of 1.40 mm, an approximate outer diameter of 1.71 mm, and a durometer of Shore 60A (Beere Precision Silicone, Racine, Wis.), was placed over the distal end of the catheter shaft 219 such that the proximal edge of the silicone tubing 123 was approximately 9.8 cm proximal from the distal end of the catheter shaft 219. This was done very carefully to ensure that no section of the silicone tubing 123 was longitudinally stretched (i.e., under tension) when at its final position on catheter shaft 219. Isopropyl alcohol was used as a lubricant between the catheter shaft 219 and the silicone tubing 123.

While the elastomeric tubing used for this example was silicone tubing, it is believed that other elastomeric tubing materials such as polyurethane tubings may also be suitably employed.

Figure 11B:
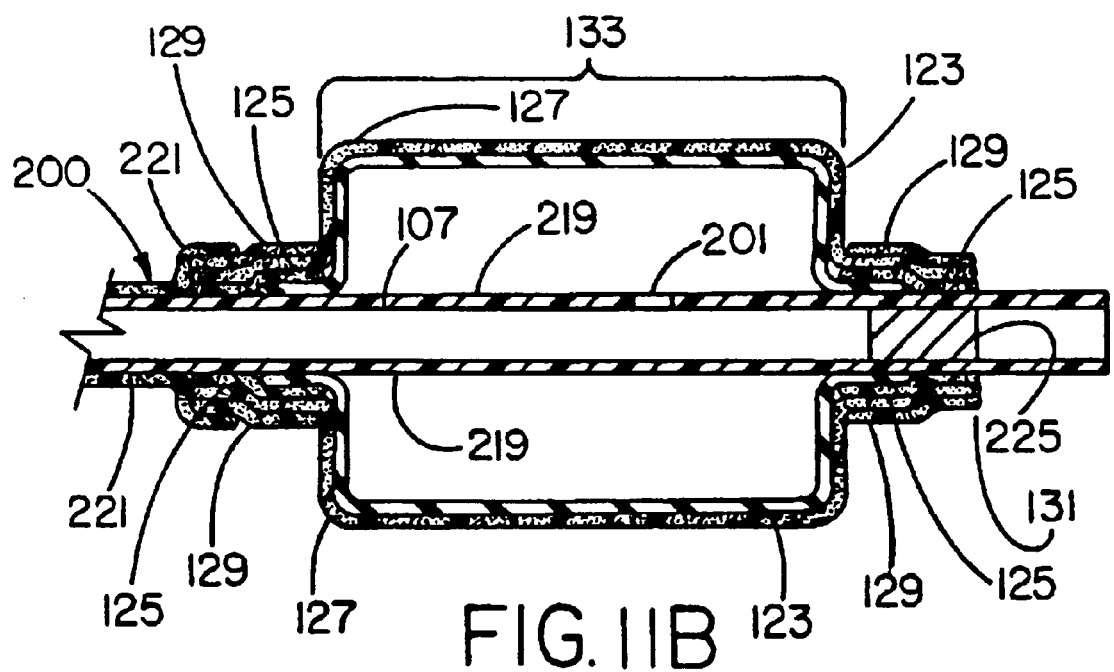

With the silicone tubing 123 placed correctly on the catheter shaft 219, any residual alcohol was allowed to evaporate for a generous amount of time, ensuring that the shaft 219 was completely dry. Once free of residual alcohol, a small amount of Medical Implant Grade Dimethyl Silicone Elastomer Dispersion In Xylene (Part 40000, Applied Silicone, Ventura, Calif.) was applied between the ends of the silicone tubing 123 and the underlying exterior surface of the silicone catheter shaft 219. At each end of the silicone tubing 123, a small blunt needle was inserted between the ends of the silicone tubing 123 and the underlying silicone catheter shaft 219 for a distance of approximately 7.5 mm as measured in a direction parallel to the length of the catheter shaft 219. The silicone elastomer dispersion was carefully applied, using a 3 cc syringe connected to the blunt needle, around the entire circumference of the shaft 219 such that the dispersion remained within, and fully coated the 7.5 mm length of the area to be bonded under the ends of the silicone tubing 123. The silicone elastomer dispersion was then allowed to cure for approximately 30 minutes at ambient temperature, and then an additional 30 minutes in an air convection oven set at 150° C. Next, a length of porous PTFE film as described above, approximately 1.0 cm wide, was manually wrapped over the end regions of the silicone tubing 123 under which the silicone elastomer dispersion was present, and onto the adjacent portions of the silicone catheter shaft 219 not covered by the silicone tubing 123, for a length of approximately 7.5 mm measured from the ends of the silicone tubing 123. During wrapping, the entire length of the porous PTFE film was coated with a small amount of the silicone elastomer dispersion. Great care was taken to ensure that the porous PTFE film was applied so that approximately 3 overlapping layers (depicted schematically as layers 125 in FIGS. 11A and 11B) covered each of the regions; the very thin porous PTFE film did not add significantly to the outside diameter of the catheter assembly 100. At this point the silicone elastomer dispersion was allowed to cure for approximately 30 minutes at ambient temperature, and then an additional 30 minutes in an air convection oven set at 150° C.

Next, a film tube was constructed in the same manner as described in Example 7. The silicone catheter shaft 219 with the silicone tubing 123 affixed to it via porous PTFE film 125 and silicone elastomer dispersion was then carefully coated with a thin layer of a mixture of 2 parts MED1137 Adhesive Silicone Type A manufactured by NuSil Silicone Technology (Carpinteria, Calif.) to 1 part n-Heptane (J. T. Baker, Phillipsburg, N.J.) by weight. The 1.76 mm inside diameter film tube was removed from the silicone-Heptane mixture, and the coated silicone catheter shaft 219 was carefully fitted coaxially within the film tube 127 such that the entire silicone tube 123 affixed to the catheter shaft 219, as well as an adjacent portion of the catheter shaft 219 proximal to both ends of the silicone tube 123, were covered by the film tube 127. With the catheter shaft 219 and the affixed silicone tube 123 covered by the film tube 127, the ends of the film tube 127 were trimmed so that the distal end of the film tube 127 was located 7.5 mm distal from the distal end of the underlying silicone tubing 123, and the proximal end was located 7.5 mm proximal from the proximal end of the underlying silicone tubing 123. The exterior surface of film tube 127 was then helically wrapped by hand with a length of 1.9 cm wide porous PTFE film, made as described above, so that about 2 overlapping layers of film covered its length. This film (not shown) was applied temporarily as a securing means desired during the subsequent heating and curing step. This distal portion of the catheter assembly 200 was then placed into a steam bath for a period of time between 15 and 30 minutes.

The catheter assembly 200 was then removed from the steam bath, and the outer helically-wrapped film layers were removed. Next, lengths of porous PTFE film as described above, approximately 1.0 cm wide were manually wrapped over the ends of the film tube 127 approximately 15 mm proximal from the distal edge of the film tube 127, and approximately 15 mm distal from the proximal edge of the film tube 127. These regions were covered by approximately 3 overlapping film layers, shown schematically as layers 129. Additionally a length of porous PTFE film (shown schematically as layer 221) was wrapped helically along the length of the catheter shaft 219 from the proximal edge of the silicone tube 123 to the Luer fitting at the proximal end of the catheter shaft 219 so that about 2 overlapping layers of film covered the catheter shaft 219, and then another 2 layers of the same film were helically wrapped over the first 2 layers at the same pitch angle (about 70 degrees) with respect to the longitudinal axis, but in the opposite direction. During wrapping, each length of porous PTFE film was coated with a small amount of a mixture of equal parts of MED1137 Adhesive Silicone Type A, manufactured by NuSil Silicone Technology (Carpinteria, Calif.), and n-Heptane (J. T. Baker, Phillipsburg, N.J.) by weight. Great care was taken to ensure that the porous PTFE film was applied without adding significantly to the catheter diameter. This was possible as a result of the thin character of the porous PTFE film. The catheter assembly 200 was then placed into a steam bath for a minimum of 8 hours to achieve curing. After curing the distal-most portion of the catheter shaft 219 was cut off transversely at the distal-most edge 131 of the porous PTFE film 129 on the exterior of the film tube 127, and the open inflation lumen 107 was sealed by insertion of a 1 cm long section of 0.38 mm wire 225 which was dipped into a mixture of equal parts of MED1137 Adhesive Silicone Type A, manufactured by NuSil Silicone Technology (Carpinteria, Calif.), and n-Heptane (J. T. Baker, Phillipsburg, N.J.) by weight. The catheter assembly 200 was then placed into a steam bath for a minimum of 8 hours to achieve final curing.

At this point, the diameter of balloon portion 133 was measured in a pre-inflated state. The minimum diameter was found to be 2.13 mm and the maximum diameter 2.28 mm. As before, these measurements were taken from approximately the midpoint of the balloon, and a Lasermike model 183, manufactured by Lasermike, (Dayton, Ohio) was used to make the measurements while the balloon was rotated about its longitudinal axis. The balloon when inflated to 8 atmospheres internal water pressure (as described by the longitudinal cross section of FIG. 11B) for a period of 1 minute or less, had a minimum diameter of 6.00 mm and a maximum diameter of 6.11 mm at the center of its length. When deflated by removing the entire volume of water introduced during the 8 atmosphere pressurization, the balloon at its mid-length had a minimum diameter of 2.16 mm and a maximum diameter of 2.64 mm. This silicone-PTFE composite balloon, when tested using a hand-held inflation device had a burst pressure of approximately 21 atmospheres (achieved beginning from zero pressure in about 30 seconds), reaching a maximum diameter of about 7.54 mm prior to failure. The balloon failed by developing a leak in the silicone tubing component 123 of the balloon portion 133. The leak caused separation between the film tube 127 and the silicone tubing 123, allowing fluid to pass through the film tube 127.

This illustrates that the balloon, constructed as described above using silicone and PTFE, exhibited a predictable limit to its diametrical growth as demonstrated by the destructive burst test wherein the balloon did not exceed the 8 mm diameter of the porous PTFE film tube component prior to failure. The compaction ratio as previously defined was 2.28 divided by 2.64, or 0.86, and the compaction efficiency ratio as previously defined was 2.16 divided by 2.64, or 0.82. Additionally, the presence of the porous PTFE film helically wrapped around the silicone catheter shaft 219 provided sufficient strength to enable the silicone catheter shaft 219 to withstand the relatively high pressures associated with angioplasty.

Another balloon was constructed in an identical manner as described above, except that the length of the silicone catheter shaft 219 from the proximal edge of the silicone tube 123 to the Luer fitting at the proximal end of the shaft 219 was not covered by porous PTFE film 221. When the balloon portion 133 was measured in a pre-inflated state the minimum diameter was found to be 2.14 mm and the maximum diameter 2.21 mm. These measurements were made as described above. The balloon when inflated to 8 atmospheres internal water pressure for a period of 1 minute or less, had a minimum diameter of 5.98 mm and a maximum diameter of 6.03 mm at the center of its length. When deflated by removing the entire volume of water introduced during the 8 atmosphere pressurization, the balloon at its mid-length had a minimum diameter of 2.10 mm and a maximum diameter of 2.45 mm. This silicone-PTFE composite balloon, when tested using a hand-held inflation device had a burst pressure of approximately 15 atmospheres, reaching a maximum dimension of about 6.72 mm prior to failure. The failure mode of the balloon was shaft rupture.

This illustrates that the balloon, constructed as described above using silicone and PTFE exhibited a predictable limit to its diametrical growth as demonstrated by the destructive burst test wherein the balloon did not exceed the 8 mm diameter of the porous PTFE film tube component prior to failure. The compaction ratio as previously defined was 2.21 divided by 2.45, or 0.90, and the compaction efficiency ratio as previously defined was 2.10 divided by 2.45, or 0.86. The absence of the porous PTFE film helically wrapped around shaft allowed the balloon to fail at the shaft. The ability of the balloon to inflate to the described pressures without water leakage demonstrated effectively that the void spaces of the porous PTFE had been substantially sealed by the elastomeric material. A flow chart describing the process used to create the balloon catheter described by this example is presented as FIG. 11C; it will be apparent that variations on this process may be used to create the same or similar balloon catheters.

EXAMPLE 9

This example describes an alternative method of creating a silicone-PTFE laminated balloon portion, and the use of the balloon portion as an angioplasty balloon.

First, a catheter shaft was constructed in the same manner as described in Example 7.

After completion of the catheter shaft, a film tube was created as follows. A length of porous PTFE film, cut to a width of 2.5 cm, made as described above, was wrapped onto the bare surface of an 8 mm stainless steel mandrel at an angle of approximately 70° with respect to the longitudinal axis of the mandrel so that about 5 overlapping layers of film covered the mandrel (i.e., any transverse cross section of the film tube transects about five layers of film). Following this, another 5 layers of the same film were helically wrapped over the first 5 layers at the same pitch angle with respect to the longitudinal axis, but in the opposite direction. The second 5 layers were therefore also oriented at an approximate angle of 70°, but measured from the opposite end of the axis in comparison to the first 5 layers. In the same manner, additional layers of film were applied five layers at a time with each successive group of five layers applied in an opposing direction to the previous group until a total of about 30 layers of helically wrapped film covered the mandrel. This film-wrapped mandrel was then placed into an air convection oven set at 380° C. for 11.5 minutes to heat bond the layers of film, then removed from the oven and allowed to cool. Once cool, the resulting film tube was removed from the 8 mm mandrel.

Next a 24 cm length of silicone tubing having an approximate inner diameter of 1.40 mm, an approximate outer diameter of 1.71 mm, and a durometer of Shore 60A (Beere Precision Silicone, Racine, Wis.) was fitted coaxially over a 1.14 mm diameter stainless steel mandrel. After one end of the silicone tubing was secured onto the mandrel by tying with thin thread, tension was applied to the other end, stretching the tubing until its overall length was 31 cm. With the tubing stretched to 31 cm the free end was also secured to the mandrel using thin thread.

The 8 mm inside diameter film tube was then manually tensioned longitudinally, causing it to reduce in diameter. The film tube was then knotted at one end, and a blunt needle was inserted into the other. Using a 20 cc syringe connected to the blunt needle, a mixture of 1 part MED1137 Adhesive Silicone Type A manufactured by NuSil Silicone Technology (Carpinteria, Calif.) to 4 parts n-Heptane (J. T. Baker, Phillipsburg, N.J.) by weight was injected into the film tube. The mixture while in the lumen of the film tube was pressurized manually via the syringe, causing it to flow through the porous PTFE, completely wetting and saturating the film tube.

Next, the 1.14 mm mandrel and the overlying silicone tubing were coated with a mixture of 2 parts MED1137 Adhesive Silicone Type A manufactured by NuSil Silicone Technology (Carpinteria, Calif.) to 1 part n-Heptane (J. T. Baker, Phillipsburg, N.J.) by weight. The blunt needle was removed from the PTFE film tube. The 1.14 mm mandrel and overlying silicone tubing were then fitted coaxially within the film tube with the ends of the film tube extending beyond the mandrel ends. The ends of the film tube were then placed into a model 4201 Tensile Testing Machine manufactured by Instron (Canton, Mass.) equipped with flat faced jaws and pulled at a constant rate of 200 mm/min until a force between 4.8 and 4.9 kg was achieved. During pulling, the film tube was massaged, ensuring contact between the PTFE and the silicone tubing. Small needle holes were made into the film tube so that the resident silicone-heptane mixture could escape. Once a force between 4.8 and 4.9 kg was achieved, the film tube was left within the jaws of the machine for a minimum of 24 hours, allowing the silicone to cure completely. Once the silicone was completely cured, the resulting silicone-PTFE composite tubing was carefully removed from the 1.14 mm mandrel.

Although this example used the silicone tubing and the porous PTFE film tube as separate substrates joined together in laminated relationship, the balloon has also been constructed using only the porous PTFE film tube made as described for example 7 and impregnated with the elastomeric material (i.e., the balloon was constructed without the silicone tubing substrate). For such a construction, the use of a silicone elastomer dispersion in Xylene is preferred as the elastomeric material intended to substantially seal the void spaces in the porous PTFE tube (i.e., wherein a substantial portion of the elastomeric material is located within the void spaces within the porous PTFE tube). The balloon so constructed was joined to the catheter shaft in the same manner described as follows. The resulting balloon had a particularly thin wall having excellent compaction efficiency ratio and compaction ratio; a balloon catheter incorporating this balloon is anticipated to be particularly useful as a neural balloon dilatation catheter.

Figure 12A:
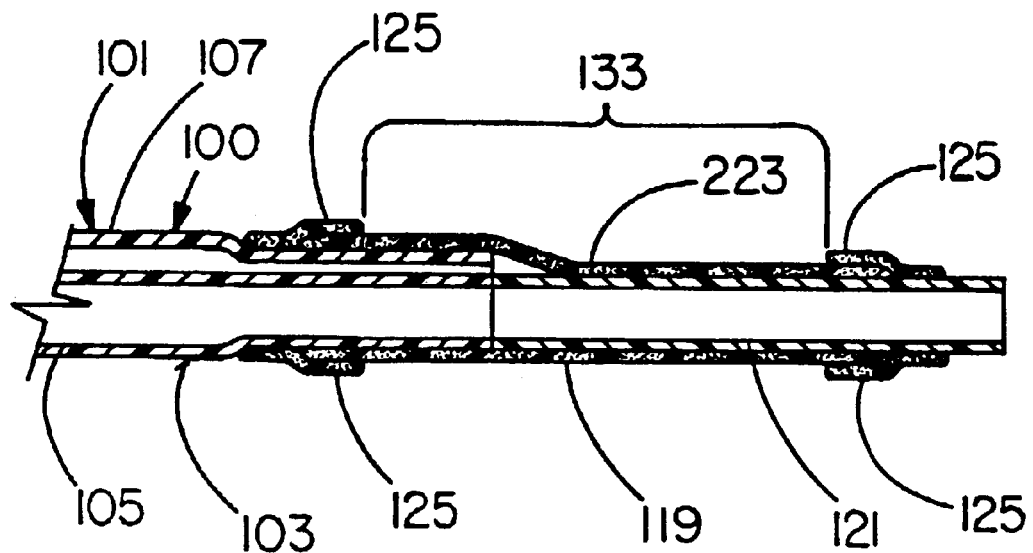

As shown by the longitudinal cross section of FIG. 12A, a segment of the silicone-PTFE composite tubing 223 (comprising the inner substrate of the elastomeric material (silicone tubing) joined to the outer substrate of the porous PTFE film tube in laminated relationship) approximately 9 cm in length was placed over the distal end of the catheter shaft 101 such that such that the proximal edge of the composite tubing 223 was approximately 7 mm distal from the point at which the catheter shaft 101 outer diameter changed from 1.83 mm to 2.3 mm. This was done very carefully to ensure that no section of the composite tubing 223 was longitudinally stretched (i.e., under tension) when at its final position on the catheter shaft 101. Isopropyl alcohol was used as a lubricant between the catheter shaft 101 and the composite tubing 223.

With the composite tubing 223 placed correctly on the catheter shaft 101, any residual alcohol was allowed to evaporate for a generous amount of time, ensuring that the catheter shaft 101 was completely dry. Once free of residual alcohol, a small amount of a mixture of equal parts of MED1137 Adhesive Silicone Type A manufactured by NuSil Silicone Technology (Carpinteria, Calif.) and n-Heptane (J. T. Baker, Phillipsburg, N.J.) by weight was applied between the ends of the tubing 223 and the underlying exterior surface of the catheter shaft 101 At each end of the silicone tubing 223, a small blunt needle was inserted between the ends of the tubing 223 and the underlying catheter shaft 101 for a distance of approximately 7.5 mm as measured in a direction parallel to the length of the catheter shaft 101. The mixture was carefully applied using a 3 cc syringe connected to the blunt needle, around the entire circumference of the catheter shaft 101 such that the mixture remained within, and fully coated the 7.5 mm length of the area to be bonded under the ends of the composite tubing 223. To ensure that the adhesive did not migrate into the inflatable length of balloon portion 133, prior to the application of the adhesive a thin thread was temporarily wrapped around composite tubing adjacent to the edge of porous PTFE film layer 125 closest to balloon portion 133. Also, to ensure contact between the composite tubing 223 and the catheter shaft 101, lengths of porous PTFE film as described above, approximately 1.0 cm wide were helically wrapped by hand over the composite tube over the areas in which the silicone mixture was applied. This film (not shown) was applied temporarily as a securing means desired during the subsequent heating and curing step. The silicone mixture was then allowed to cure within a steam bath for approximately 30 minutes. The catheter was then removed from the steam bath, and the 1.0 cm wide PTFE film was removed along with the temporary thread.

Figure 12B:
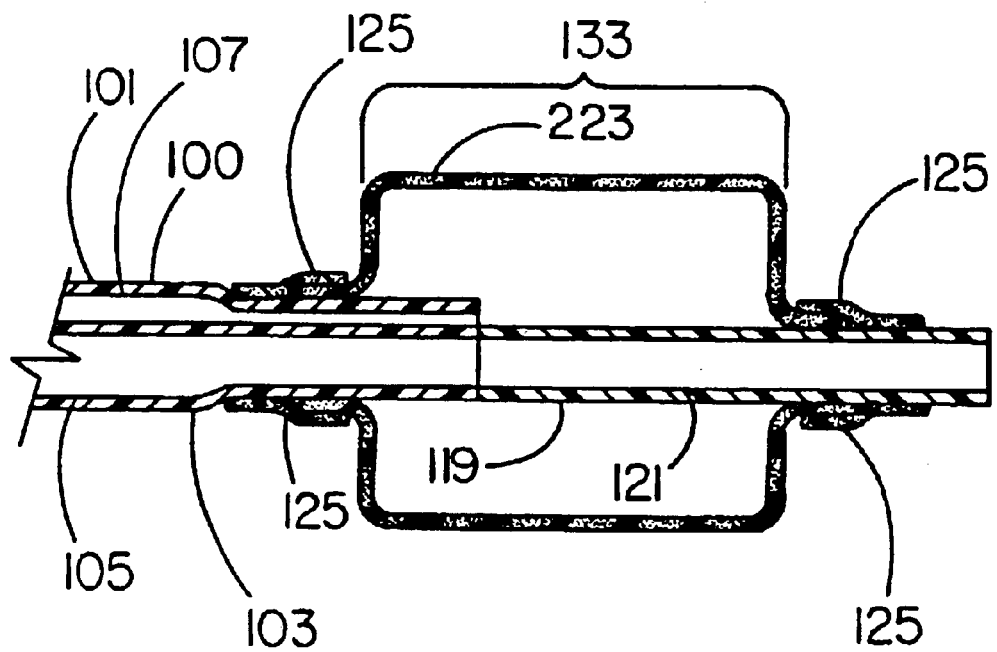

Next, a length of porous PTFE film as described above, approximately 1.0 cm wide was manually wrapped over the end regions of the composite tubing 223 under which the silicone mixture was present, and onto the adjacent portions of the catheter shaft 101 not covered by the composite tube 223, for a length of approximately 7.5 mm measured from the ends of the composite tubing 223. During wrapping, the entire length of the porous PTFE film was coated with a small amount of a mixture of equal parts of MED1137 Adhesive Silicone Type A manufactured by NuSil Silicone Technology (Carpinteria, Calif.) and n-Heptane (J. T. Baker, Phillipsburg, N.J.) by weight. Great care was taken to ensure that the porous PTFE film was applied so that approximately 3 overlapping layers (depicted schematically as layers 125 in FIG. 12) covered each of the regions without adding significantly to the diameter of the catheter. Because of the reduced diameter region at the distal end of dual lumen tubing 103 and the very thin character of the porous PTFE film used for layers 125, the diameter of the catheter assembly 100 at the location of film layers 125 was very close to the diameter of catheter shaft 101 proximal to film layers 125. Finally, the silicone mixture used to coat the porous PTFE film was allowed to cure for a minimum of 8 hours within a steam bath.

At this point, the diameters of the balloon portion 133 were measured in a pre-inflated state using the same methods described above. The minimum diameter was found to be 2.21 mm and the maximum diameter 2.47 mm. The balloon when inflated to 8 atmospheres internal water pressure (as described by the longitudinal cross section of FIG. 12B) for a period of 1 minute or less, had a minimum diameter of 6.51 mm and a maximum diameter of 6.65 mm at the center. It was noted during the 8 atmosphere pressurization that the balloon portion was substantially straight with respect to the longitudinal axis of the catheter shaft, and that the distance from the point at which the balloon portion was attached to the catheter shaft to the point on the balloon portion at which the balloon was at its full diameter was relatively short. When deflated by removing the entire volume of water introduced during the 8 atmosphere pressurization, the balloon at its mid-length, had a minimum diameter of 2.28 mm and a maximum diameter of 2.58 mm. This silicone-PTFE composite balloon, when tested using a hand-held inflation device, had a burst pressure of approximately 15 atmospheres (achieved beginning from zero pressure in about 30 seconds), reaching a maximum diameter of about 7.06 mm prior to failure.

This example illustrates that the balloon, constructed as described above using a silicone-PTFE composite balloon portion, exhibited a predictable limit to its diametrical growth as demonstrated by the destructive burst test wherein the balloon did not exceed the 8 mm diameter of the porous PTFE film tube component. The compaction ratio as previously defined was 2.47 divided by 2.58, or 0.96, and the compaction efficiency ratio as previously defined was 2.28 divided by 2.58, or 0.88. The ability of the balloon to inflate to the described pressures without water leakage demonstrated effectively that the void spaces of the porous PTFE had been substantially sealed by the elastomeric material.

A flow chart describing the process used to create the balloon catheter described by this example is presented as FIG. 12C; it will be apparent that variations on this process may be used to create the same or similar balloon catheters.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. A method of installing a stent within a patient's body, comprising:
   a) providing a catheter system, comprising:
      i) a tubular catheter shaft having a longitudinal axis with a proximal end and a distal end, said catheter shaft having an inflation lumen extending from an inflation port and extending distally to a location proximally spaced from the distal end;
      ii) an inflatable balloon affixed near the distal end of the catheter shaft, said balloon having an interior chamber in fluid communication with the inflation lumen, wherein said balloon is formed of a polyurethane, wherein said balloon has a preinflated shape, said shape having a substantially circular cross-section; and wherein said balloon has opposing ends affixed to the catheter shaft, said balloon having a length measured between said opposing ends, wherein the length varies less than ten percent between when the balloon is in a deflated state and when the balloon is inflated to a pressure of 8 atmospheres; and
      iii) an expandable stent disposed about and mounted onto the balloon;
   b) inserting the catheter system into the patient's body;
   c) inflating the balloon to produce radial expansion of the balloon and the stent mounted thereon; and
   d) deflating the balloon to its preinflated shape.

2. The method of claim 1, wherein the balloon length varies less than five percent between when the balloon is in a deflated state and when the balloon is inflated to a pressure of 8 atmospheres.

3. A method of installing a stent within a patient's body, comprising:
   a) providing a catheter system, comprising:
      i) a tubular catheter shaft having a longitudinal axis with a proximal end and a distal end, said catheter shaft having an inflation lumen extending from an inflation port and extending distally to a location proximally spaced from the distal end;
      ii) an inflatable balloon affixed near the distal end of the catheter shaft, said balloon having an interior chamber in fluid communication with the inflation lumen, wherein said balloon is formed of polymeric material; wherein said balloon has a preinflated shape, said shape having a substantially circular cross-section; wherein said balloon has opposing ends affixed to the catheter shaft, said balloon having a length measured between said opposing ends, wherein the length varies less than ten percent between when the balloon is in a deflated state and when the balloon is inflated to a pressure of 8 atmospheres; and
      iii) an expandable stent disposed about and mounted onto the balloon;
   b) inserting the catheter system into the patient's body;
   c) inflating the balloon to produce radial expansion of the balloon and the stent mounted thereon; and
   d) deflating the balloon to its preinflated shape.

4. The method of claim 3, wherein the balloon length varies less than five percent between when the balloon is in a deflated state and when the balloon is inflated to a pressure of 8 atmospheres.

* * * * *